(12) United States Patent
Couture et al.

(10) Patent No.: US 7,365,190 B2
(45) Date of Patent: Apr. 29, 2008

(54) CROSSLINKED POLYSACCHARIDE, OBTAINED BY CROSSLINKING WITH SUBSTITUTED POLYETHYLENE GLYCOL, AS SUPERABSORBENT

(75) Inventors: Claude Couture, Westmount (CA); David Bergeron, Longueuil (CA); Frédéric Picard, Longueuil (CA)

(73) Assignee: Archer-Daniels-Midland Company, Decatur, IL (US)

( * ) Notice: Subject to any disclaimer, the term of this patent is extended or adjusted under 35 U.S.C. 154(b) by 422 days.

(21) Appl. No.: 10/044,846

(22) Filed: Nov. 9, 2001

(65) Prior Publication Data

US 2003/0027787 A1 Feb. 6, 2003

(30) Foreign Application Priority Data

Nov. 10, 2000 (CA) .................................. 2325643
Jun. 26, 2001 (CA) .................................. 2351253

(51) Int. Cl.
C07H 1/00 (2006.01)
C08G 63/00 (2006.01)
A61Q 1/00 (2006.01)

(52) U.S. Cl. ..................... 536/123.1; 527/300; 536/84; 536/111; 424/69

(58) Field of Classification Search ................. 536/45, 536/50, 123.1, 84, 111; 424/69; 522/88; 527/300, 315
See application file for complete search history.

(56) References Cited

U.S. PATENT DOCUMENTS

| | | | |
|---|---|---|---|
| 2,148,951 A | 2/1939 | Maxwell | |
| 2,383,091 A | 8/1945 | Toussaint et al. | |
| 2,461,139 A | 2/1949 | Caldwell | |
| 3,753,931 A | 8/1973 | Raspanti | |
| 3,941,771 A | 3/1976 | Finley | |
| 4,029,590 A | 6/1977 | Finley | |
| 4,117,222 A | 9/1978 | Holst et al. | |
| 4,237,271 A | 12/1980 | Rayford et al. | |
| 4,278,658 A * | 7/1981 | Hooper et al. | 424/65 |
| 4,296,234 A * | 10/1981 | Mindt et al. | 536/47 |
| 4,508,705 A * | 4/1985 | Chaudhuri et al. | 424/47 |
| 5,079,354 A | 1/1992 | Gross et al. | |
| 5,264,495 A * | 11/1993 | Irie et al. | 525/301 |
| 5,360,903 A | 11/1994 | Lane et al. | |
| 5,550,189 A * | 8/1996 | Qin et al. | 525/54.3 |
| 5,789,570 A | 8/1998 | Buchholz et al. | |
| 6,063,914 A | 5/2000 | Wolf et al. | |

FOREIGN PATENT DOCUMENTS

| | | |
|---|---|---|
| EP | 1 134 232 A1 | 9/2001 |
| GB | 1508511 | 4/1978 |
| WO | WO 95/31500 | 11/1995 |
| WO | WO 97/15367 | 5/1997 |
| WO | WO 00/21581 | 4/2000 |
| WO | WO 00/35504 | 6/2000 |
| WO | WO 00/67809 | 11/2000 |

OTHER PUBLICATIONS

Riccardo Po, Water-Absorbent Polymers: a patent survey, *J. Macromol. Sci., Rev. Macromol. Chem. Phys.*, 1994, pp. 607-662.
Buchholz, et al., ed., *Modern Superabsorbent Polymer Technology*, Wiley-VCH, Toronto, 1998, pp. 239-241.
Anbergen, et al., Elasticity and swelling behaviour of chemically crosslinked cellulose ethers in aqueous systems, *Polymer*, v. 31, Oct. 1990, pp. 1854-1858.
Fusako Kawai, The biochemistry of Degradation of Polyethers, *Crit. Rev. Biotech*, v.6, Issue 3, 1987, pp. 273-307.
Matsumura, et al., Microbial transformation of poly(ethylene glycol)s into mono- and dicarboxylic derivatives by specific oxidation of hydromethyl groups, *Makromol. Chem. Rapid Comm.*, No. 20, 1989, pp. 63-67.
U.S. Environmental Protection Agency (EPA) Prevention, Pesticides, and Toxic Substances (7101), *Fate, transport and transformation test guidelines (OPPTS 835.3200 Zahn-Wellens/EMPA test)*, EPA712-C-98-084, Jan. 1998.
Rayford, et al., Crosslinked cationic and anionic starches: preparation and use in heavy metal removal, *Starch/Stärke*, No. 31, 1979, pp. 361-365.
Robert E. Wing, Starch Citrate: preparation and ion exchange properties, *Starch/Stärke*, No. 48, 1996, pp. 275-279.
Wepner, et al., Citrate Starch—application as a resistant starch in different food system, *Starch/Stärke*, No. 51, 1999, pp. 354-361.
Tijsen, et al., An experimental study on the carboxymethylation of granular potato starch in non-aqueous media, *Carbohydrate Polymers;*, Elsevier Science Ltd., No. 45, 2001, pp. 219-226.
Trimnell, et al., Preparation of starch 2-hydroxy-3-mercaptopropyl ethers and their use in graft polymerizations, *Journal of Applied Polymer Science*, v. 22, 1978, pp. 3579-3586.
Zhu, et al., Crosslinked quaternary ammonium cornstarch matrix for slow release of carboxylic groups—containing herbicides, *Starch/Stärke*, No. 52, 2000, pp. 58-63.
Edana, *Recommended Test Method: Superabsorbent material—polyacrylate superabsorbent powders—Centrifuge retention in capacity in saline by gravimetric determination*, 441. 1-99, Feb. 1999.

* cited by examiner

*Primary Examiner*—Thao Tran
(74) *Attorney, Agent, or Firm*—Fay Sharpe LLP

(57) ABSTRACT

New crosslinked polysaccharides useful as absorbents or superabsorbents alone or in a mixture are obtained by reacting polysaccharides (preferably containing carboxylates groups) with at least one crosslinker selected in the group constituted by activated polyethylene glycols such as for example halogenated (Cl, Br, I), mesylated, tosylated, or triflated activated polyethylene glycols.

23 Claims, 6 Drawing Sheets

Figure 1:
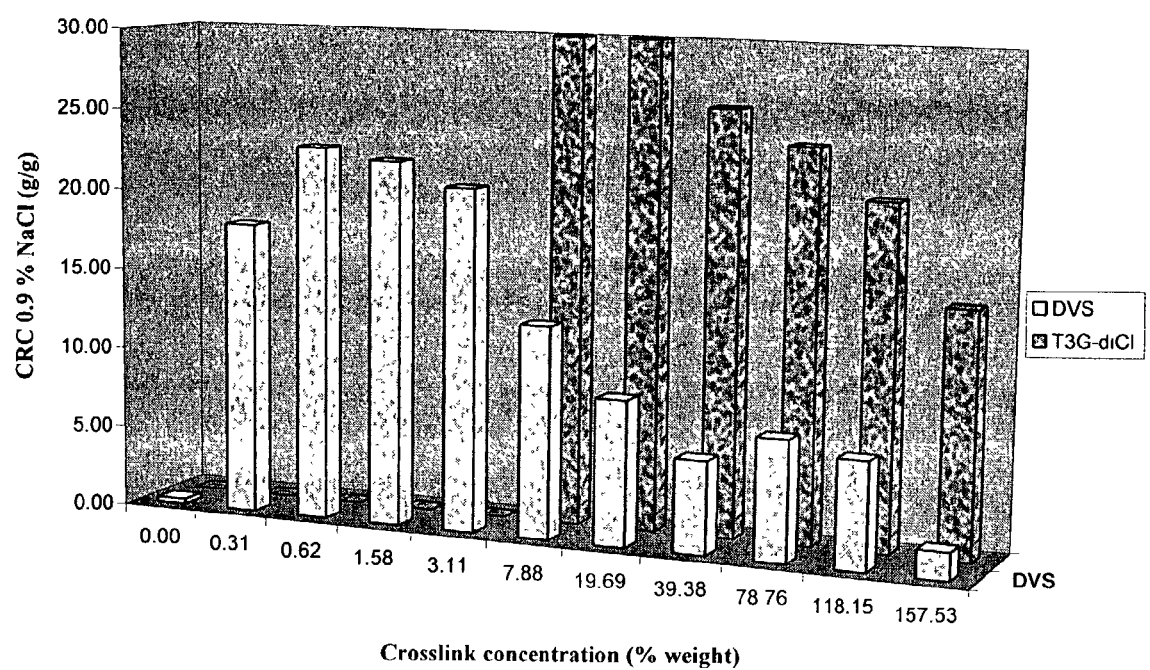

CROSSLINKED POLYSACCHARIDE, OBTAINED BY CROSSLINKING WITH SUBSTITUTED POLYETHYLENE GLYCOL, AS SUPERABSORBENT

The present invention relates to a cross-linked polysaccharide(s) which is (are) useful as an absorbent(s) or superabsorbent(s); such cross-linked polysaccharide(s) may be exploited either alone or in a mixture with one or more other absorbent components, e.g. with absorbents of the same or different type as well s other desired or necessary components. The present invention also relates to cross-linked polysaccharides which are biodegradable. The present invention further relates to a process(es) for preparing such cross-linked polysaccharide(s); such process may for example exploit one or more relatively inexpensive cross-linking agents.

BACKGROUND OF THE INVENTION

The polysaccharides are a group of carbohydrates composed of long chains of simple sugars, such as for example, starch, cellulose, dextrins, polygalactomannans, chitin, chitosan, alginates, xanthan gum, carageenan gum, gum karaya, gum Arabic, pectin and glass-like polysaccharides as well as other derivatives thereof such as ionic and/or non-ionic derivatives. Examples of starches are: corn, wheat, rice, potato, tapioca, waxy maize, sorghum, waxy sorghum, sago and modified starches such as dextrinated, hydrolysed, oxidized, crosslinked, alkylated, hydroxyalkylated, acetylated, fractionated (e.g. amylose and amylopectin), and physically modified starches.

Polysaccharides have been exploited as absorbent or superabsobents with respect to the uptake of aqueous substances (e.g. water, etc.).

Superabsorbent polysaccharide-based polymers may be obtained through grafting of an unsaturated monomer (acrylonitrile, acrylic acid, acrylamide) onto starch or, less frequently, cellulose. These polymers also called "Super Slurper" showed water absorption from 700 to 5,300 g/g for deionised water and up to 140 g/g in saline solution (Riccardo PO, Water-Absorbent Polymers: A Patent Survey. *J. Macromol. Sci., Rev. Macromol. Chem. Phys.*, 1994, 607-662 (p.634) and cited references). Despite their very high water absorption, these grafted polysaccharides, prepared by radical polymerization are not known to be biodegradable.

Carboxymethylcellulose (CMC) having the following formula

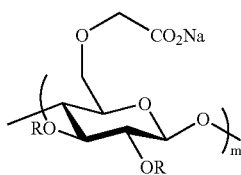

R=H, carboxymenthyl m is an integer of from 100 to 12,000 is a known polysaccharide-based superabsorbent which is commercially available from numerous vendors (*Modern Superabsorbent Polymer Technology*, Buchholz F. L. and Graham A. T. ed., Wiley-VCH, Toronto, 1998, pages-239-241 and cited references).

Carboxymethylstarch (CMS) having the following formula

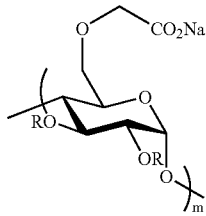

R=H carboxymethyl m is an integer of from 1000 to 3 million for (natural) starches is another known polysaccharide-based superabsorbent which is also commercially available from numerous vendors are among known polysaccharide-based superabsorbents (Gross and Greuel, U.S. Pat. No. 5,079,354, Jan. 7, 1992, 536/111).

Anbergen and Oppermann have studied the elasticity and the swelling behaviour of sodium carboxymethylcellulose and hydroxyethylcellulose, chemically crosslinked with divinylsulfone (Andergen U. and Oppermann W., Elasticity and swelling behaviour of chemically crosslinked cellulose ethers in aqueous systems. *Polymer*, 1990, 31, 1854-1858).

Kabra and Gehrke (WO 95/31500, Nov. 23, 1995, C08J. 9/28) have reported the sorption capacity of hydroxypropylcellulose, crosslinked with different concentration of divinylsulfone (from 0.28 to 2.98 weight %). The best results showed a water sorption capacity of 44 g/g with a crosslink of 0.91 weight %. The authors also mention that other hydrophobically modified carbohydrate polymers can be chosen, such as hydroxypropylstarch.

More recently, SCA Hygiene Products AB (Annergren and Lundstrom. WO 00/21581, Apr. 20, 2000, A61L 15/28, 15/60) extended the study with divinylsulfone to low-cost, readily available, renewable starting materials such as carboxymethylcellulose, carboxymethylstarch, and others.

According to the authors, results may be obtained with a mixture of carboxymethylcellulose: hydroxyethylcellulose (3:1) which absorbs close to 95 g of synthetic urine per g of polymer after free swelling for 120 min. In this patent, however, the quantity of divinylsulfone used is not reported. Divinylsulfone has been applied with respect to other polysaccharides containing acidic groups (Thornton et al. WO 00/35504, Jun. 22, 2000, A61L 15/60, 15/28.). It appears that the best result was obtained with carboxymethylcellulose crosslinked with 14 mol % of divinylsulfone. This results in a centrifuge retention capacity (CRC) of 111 g/g with synthetic urine. On page 6 of WO 00/35504 it has been mentioned that the superabsorbent polysaccharides combine high absorption capacity with control of bacterial growth and control of odour, as well as with biodegradability. There is however no evidence that such compounds would be biodegradable.

Starch ethers have been crosslinked with numerous other bifunctional groups such as acrylamido, chloroazomethine, allyloxy-azomethine groups to give absorbent materials (Holst et al., U.S. Pat. No. 4,117,222, Sep. 26, 1978, 536/50).

There is still a continuing need for environmentally safe and economical producible polysaccharide-based absorbents and superabsorbents and in particular polysaccharide-based absorbents and superabsorbents with at least a significant biodegradability.

Accordingly it would be advantageous to be able to make a cross-linked polysaccharide (and in particular a cross-linked starch) by exploiting a cross-linking agent(s) giving rise to a cross-linked product having desirable water absorption properties. It would in particular be advantageous to be able to make a cross-linked polysaccharide (and in particular a cross-linked starch) by exploiting a relatively cheap cross-linking agent(s). It would further be advantageous to be able to to be able to make a cross-linked polysaccharide (and in particular a cross-linked starch) by exploiting a cross-linking agent(s) giving rise to a cross-linked product having desirable biodegradability properties.

STATEMENT OF INVENTION

The present invention in one aspect relates to a cross-linked polysaccharide(s) (e.g. a cross-linked starch), said cross-linked polysaccharide(s) (e.g. a cross-linked starch), being a polysaccharide (e.g. starch) cross-linked by an ether linkage consisting of a backbone chain of atoms, said backbone chain of atoms consisting of two terminal ether oxygen atoms, one or more intermediate oxygen link atoms and two or more —CH$_2$— link groups, each oxygen link atom being an ether oxygen atom. The backbone chain of atoms may thus be considered to have the formula 1

1 wherein said Linker consists of one or more intermediate ether oxygen link atoms and two or more —CH$_2$— link groups (e.g. the Linker may be —CH$_2$—O—CH$_2$—); as may be seen the backbone chain of atoms of formula 1, (in addition to the Linker), includes two terminal oxygen atoms spaced apart by the Linker, these terminal oxygen atoms are the terminal ether oxygen atoms referred to above. Please see for example the compound of formula 9 below which illustrates the incorporation of a backbone chain of atoms into a cross-linked starch half ester; as may be seen from formula 9 the terminal oxygens are connected to the starch residues as ether oxygens.

The present invention in particular relates to a cross-linked polysaccharide(s) (e.g. a starch) wherein the cross-linkage is an above described ether linkage, said backbone chain of atoms comprising at least one —O-Alkylene- group, wherein Alkylene comprises one or more —CH$_2$— groups; Alkylene may more particularly comprise from 1 to 5 —CH$_2$— groups (e.g. Alkylene may be methylene (i.e. —CH$_2$—), ethylene (i.e. —CH$_2$CH$_2$—), n-propylene (i.e. —CH$_2$CH$_2$CH$_2$—), etc. . . . ). More particularly the backbone chain of atoms may have the formula 2

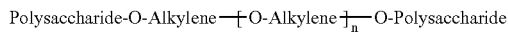

2 wherein each Alkylene is as defined above (e.q. consists of one or more —CH$_2$— groups), wherein the two terminal oxygen atoms are ether oxygen atoms, and n is an integer of from 1 to 1000 (e.q. n may be an integer of from 1 to 100, for example n may be 1, 2 or 3).

A backbone chain of atoms is to be unsubstituted as indicated above. However, a backbone chain of atoms may if so desired be substituted by one or more —CH$_3$ and/or —CH$_2$CH$_3$ groups; e.g. an Alkylene group may if so desired be substituted by one or more —CH$_3$ and/or —CH$_2$CH$_3$ groups; if desired other higher alky groups may be used as substituents.

The present invention more particularly relates to a cross-linked polysaccharide (e.g. a cross-linked starch), wherein the cross-linkage is an above described ether linkage, said backbone chain of atoms comprising at least one —O—CH$_2$—CH$_2$— group; for example, a polysaccharide (e.g. starch) cross-linked by an above described ether linkage may comprise two, three or four —O—CH$_2$—CH$_2$— groups in the backbone chain of atoms.

In accordance with the present invention the degree of cross-linking is to be chosen keeping in mind the purpose thereof, namely to achieve an absorbent material. The degree of cross-linking may be chosen on the basis of suitable experimentation. It may for example be sufficient to get a high CRC (as discussed herein) with high gel strength values. For example a quantity as low as 0.02 g of triglycol dichloride may be used to obtain a hard gel superabsorbent with a CRC of 39 g/g. The degree of cross-linking may be determined using NMR techniques.

The present invention in accordance with an other aspect provides a process for the preparation of a cross-linked polysaccharide (e.g. cross-linked starch), said cross-linked polysaccharide being a polysaccharide (e.g. a starch) cross-linked by an ether linkage consisting of a backbone chain of atoms, said backbone chain of atoms consisting of two terminal ether oxygen atoms, one or more intermediate oxygen link atoms and two or more —CH$_2$— link groups, each oxygen link atom being an ether oxygen atom (i.e. a backbone chain of atoms of formula 1 above), said process comprising the step of contacting a polysaccharide (e.g. a starch) with at least one cross-linking agent selected in the group consisting of activated polyalkylene glycols of formula 1a

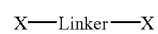

1a so as to obtain said cross-linked polysaccharide (e.g. cross-linked starch), wherein said Linker is as defined above (i.e. consists of one or more intermediate ether oxygen link atoms and two or more —CH$_2$— link groups (e.g. the Linker may be —CH$_2$—O—CH$_2$—)), and each X group is a group able to react with an alcohol hydroxyl group of said polysaccharide (e.g. starch) so as to provide an ether oxygen atom link.

The present invention in particular a process for the preparation of a cross-linked polysaccharide (e.g. cross-linked starch), said cross-linked polysaccharide being a polysaccharide (e.g. a starch) cross-linked by an ether linkage consisting of a backbone chain of atoms, said backbone chain of atoms consisting of two terminal ether oxygen atoms, one or more intermediate oxygen link atoms and two or more —CH$_2$— link groups, each oxygen link atom being an ether oxygen atom (i.e. a backbone chain of atoms of formula 2 above), said process comprising the step of contacting a polysaccharide (e.g. a starch) with at least one cross-linking agent selected in the group consisting of activated polyalkylene glycols of formula 2a

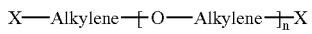

$$X—Alkylene—[O—Alkylene—]_n X \quad 2a$$

so as to obtain said cross-linked polysaccharide (e.g. cross-linked starch), wherein each Alkylene is as defined above (i.e. each Alkylene comprises or consists of one or more —$CH_2$— groups (for example each Alkylene may consist of from 1 to 5 —$CH_2$— groups (e.g. Alkylene may as mentioned above be methylene (i.e.—$CH_2$—), ethylene (i.e. —$CH_2CH_2$—), n-propylene (—$CH_2CH_2CH_2$—), etc. . . . )) each X group is as defined above (i.e. each X group is a group able to react with an alcohol hydroxyl group of said polysaccharide (e.g. starch)) so as to provide an ether oxygen atom link and n is as defined above (i.e. n is an integer of from 1 to 1000, e.g. 1 to 100).

A mixture of two or more different cross-linking agents as described herein may of course be used instead of just one linking agent.

For the above formulae 1a and 2a, as well as for other activated glycols as described herein, each X may, for example, be the same; similarly each Alkylene may, for example, be the same. Each X may for example be selected from the group consisting of halogen (e.g. Cl, Br, I), —O-Ms, —O-Ts, and —O-Tf, wherein Ms is $CH_3SO_2$—, Ts is p—$CH_3C_6H_4SO_2$— and Tf is $CF_3SO_2$—.

The reference to an "alcohol hydroxyl group" of a polysaccharide (e.g. starch) is to be understood herein as being a reference to an hydroxyl group linked to a methylene type group (i.e. a primary alcohol —$CH_2$—OH, or a secondary alcohol =CH—OH, the alcohol hydroxyl group being underlined) as distinct, for example, from an "acid hydroxyl group" linked to a carbonyl group (i.e. —CO—OH, the acid hydroxyl group being underlined).

The reference to a "starch" is to be understood herein as being a reference to starch (i.e. to a starch per se such as for example wheat starch) as well as to modified starch such as for example carboxyalkyl starch, starch maleate half-ester (as described herein) and the like.

The activated polyalkylene (e.g. polyethylene) glycols may for example be any polyfunctional glycol having any suitable (known) types of reactive functional groups able to provide cross-linkage between polysaccharide (e.g. starch) components, e.g. such as, for example, terminal halogen substituted glycols as described herein. The activated polyalkylene (e.g. polyethylene) glycol compounds of formula 1a may, for example, have an average molecular weight up to 10,000, for example up to 300 (such as from about 100 to about 300).

A process of the present invention is of course to be carried out under conditions which favour cross-linkage; for example, the process is to be carried out under basic conditions sufficient to facilitate the cross linkage but avoid the hydrolysis of any hydrolysis susceptible functional groups which may be attached to the polysaccharide (e.g. starch)

A cross-linked polysaccharide (e.g. cross-linked starch) as described herein may, for example, be obtained by reacting a polysaccharide such as for example a starch (preferably containing one or more carboxylates groups) with at least one cross-linking agent selected in the group constituted by halogenated (e.g. Cl, Br, I), mesylated, tosylated, or triflated polyethylene glycol, for example a compound of formula 1a above wherein each Alkylene is —$CH_2$—$CH_2$— and each X is selected from the group consisting of halogen (e.g. Cl, Br, I), —O—Ms, —O—Ts, and —O-Tf, wherein Ms is $CH_3SO_2$—, Ts is p-$CH_3C_6H_4SO_2$— and Tf is $CF_3SO_2$—.

The cross-linked polysaccharides (e.g. starches) according to the invention may be characterized by O-alkylation on the primary hydroxyl groups of the polymeric unit, then on the secondary hydroxyl groups at C2 or C3 carbon atoms of the polysaccharide (e.g. starch).

In accordance with the present invention a cross-linked polysaccharides may be prepared by a process exploiting one or more relatively inexpensive cross-linking agent(s) (e.g. 1,5-dichloro-3-oxopentane (i.e. a dichloropolyethylene oxide)). Preferred cross-linking agents are 1,5-dichloro-3-oxopentane, 1,8-dichloro-3,6-dioxooctane, 1,11-dichoro-3,6,9-trioxoundecane as well as homologous dichloro polyethylene glycol compounds with an average molecular weight up to 10,000.

The polysaccharide(s) (e.g. starch) may have a non-ionic or ionic characteristic, e.g. the polysaccharide (e.g. starch) may have an anionic or cationic characteristic. The polysaccharide(s) may if desired or necessary contain any suitable or desired carboxyalkyl groups keeping in mind the cross-linking aspect as well as absorbent characteristic; in particular, for example, carboxyalkyl groups wherein the alkyl moiety thereof comprises from 1 to 18 carbon atoms e.g. 1 to 3 carbon atoms.

Preferred polysaccharides are anionic and contain carboxyalkyl groups (preferably carboxymethyl groups) or half-ester prepared with maleic, succinic, sulfosuccinic, citraconic, glutaric or phthalic anhydride, where maleic anhydride is preferred. Anionic polysaccharides also include dicarboxylates such as iminodiacetate groups and tricarboxylates such as citrate groups.

Examples of polysaccharides as starting materials are: starch, cellulose, dextrins, polygalactomannans and more ionic and/or non-ionic derivatized, chitin, chitosan, and derivatives thereof, alginates, xanthan gum, carageenan gum, gum karaya, gum Arabic pectin and glass-like polysaccharides. Examples of starches are starches from: corn, wheat, rice, potato, tapioca, waxy maize, sorghum, waxy sorghum, sago and modified starches such as dextrinated, hydrolysed, oxidized, alkylated, hydroxyalkylated, acetylated, fractionated (e.g. amylose and amylopectin), and physically modified starches.

The present invention further relates to the use of a polysaccharide cross-linked as described herein as a biodegradable absorbent or superabsorbent and or/and as a hypoallergenic absorbent or superabsorbent; a superabsorbent being for example an absorbent having an absorption capacity with respect to of saline solution of higher than 15 g water/g cross-linked polymer.

The present invention additionally relates to absorbent mixtures comprising at least one cross-linked polysaccharide (e.g. cross-linked starch) as described herein and, if so desired one or more othere known absorbents/superabsorbents such as CMC, polyacrylates, etc.

A cross-linked polysaccharide or mixture thereof in accordance with the present invention may be used as an absorbent and in particular as a superabsorbent; such a cross-linked polysaccharide or mixture thereof may, for example, be incorporated into (i.e. contained in) absorbent personal hygiene products such as, for example, baby diapers, incontinence products, sanitary napkins, tampons and the like.

A cross-linked polysaccharide or mixture thereof in accordance with the present invention may be used in several other applications such as for example: food pad; telecommunication cable wrappings (for non-biodegradable polymer); in agricultural and forestry applications to retain water in soil and to release water to the roots of plants; in fire-fighting techniques; bandages and surgical pads; for cleanup of acidic or basic aqueous solutions spills, including water soluble chemicals spills and; as polymeric gels for cosmetics and pharmaceuticals also known as drug delivery systems and slow release substances and; for artificial snow.

In the following specific reference will be made to polyethylene glycol as well as to derivatives thereof, in particular activated derivatives thereof; however, it is to be understood of course that other polyalkylene glycols as well as other ether type cross-linking agents are contemplated in the context of the present invention keeping in mind that the linking agent is to be chosen so as to provide an unsubstituted backbone chain of atoms or if so desired a backbone chain of atoms substituted by one or more —$CH_3$ and/or —$CH_2CH_3$ groups.

Cross-linkers (i.e. cross-linking agents) used to prepare cross-linked starches of the invention may for example be chosen from among activated polyethylene glycols with average molecular weight varying from 100 to 10,000 and preferably from 100 to 300.

Polyethylene glycol may have the structure as set forth in general formula 2b below

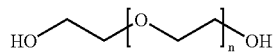

2b n=1 to 1,000 and $M_n$=up to 10,000 (e.g. 100 to 300-10,000)

Mn=average molecular weight

Polyethylene glycols are known to be biodegradable aerobically and anaerobically (Kawai F., The Biochemistry of Degradation of Polyethers. *Crit. Rev. Biotech.*, 1987, 6, 273-307) and the microbial oxidation of diethylene glycol and polyethylene glycol with the average molecular weights of 200, 400, 600, 1000 and 2000 have been reported (Matsumura S. et al. Microbial transformation of poly (ethylene glycol)s into mono- and dicarboxylic derivatives by specific oxidation of the hydroxymethyl groups. *Makromol. Chem. Rapid Commun.*, 1989, 10, 63-67.

The crosslinked polysaccharides according to the present invention may be obtained by reacting polysaccharides such as for example starch (preferably containing carboxylates groups) with at least one activated polyethylene glycol wherein the terminal hydroxyl groups are replaced by Cl, Br, I, mesylates, tosylates or triflates.

A preferred embodiment of the invention is constituted by crosslinking starches with at least one activated polyethylene glycol of formula 3 below

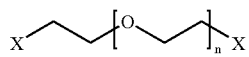

3

X=Cl, Br, I, OMs, OTs, OTf n is an integer of from 1 to 1,000 and $M_n$=100 to 10,000

$M_n$=average molecular weight

Ms=mesylate ($CH_3SO_2$—)

Ts=tosylate (p-toluenesulfonate, p-$CH_3C_6H_4SO_2$—)

Tf=triflate ($CF_3SO_2$—)

As a matter of exemplification, starches crosslinked with polyglycol dichloride (such as for example diglycol dichloride of formula 3 wherein each X is Cl and n is 1 (herein after referred to as diglycol dichloride 3a), triglycol dichloride of formula 3 wherein each X is Cl and n is 2 (hereinafter referred to as triglycol dichloride 3b), tetraglycol dichloride of formula 3 wherein each X is Cl and n is 3 (hereinafter referred to as tetraglycol dichloride 3c), are preferred; i.e. since starch is a renewable and inexpensive starting material and some polyglycol dichlorides are commercially available or easily prepared from polyethylene glycol of formula 2b above by reaction at reflux with thionyl chloride in benzene or dichloromethane in the presence of pyridine.

In accordance with the present invention a starch half ester may be cross-linked by an activated polyethylene glycol; an example of such a starch half ester cross-linked with a polyethylene glycol as set forth in formula 9 below

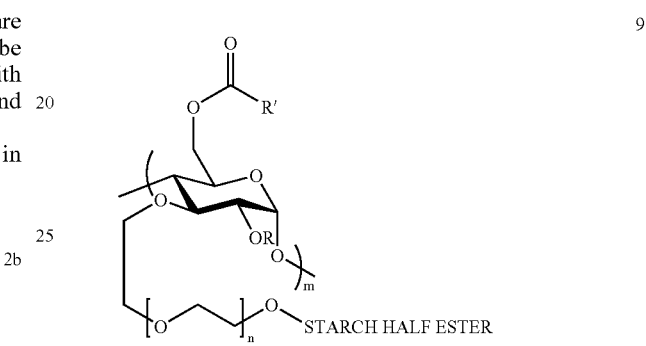

9

R=H, half ester, crosslink n is an integer of from 1 to 1,000 m is an integer of from 1000 to 3 million for (natural) starches

R' may for example be selected from the group comprising —CH=$CHCO_2Na$, —$CH_2CH_2CO_2Na$, —CH=C($CH_3$)$CO_2Na$, —C($CH_3$)=$CHCO_2Na$, —($CH_2$)$_3CO_2Na$, —(o—$CO_2Na$)$C_6H_4$, —CH($SO_3Na$)$CH_2CO_2Na$, or —$CH_2$CH($SO_3Na$)$CO_2Na$, etc.

A starch half ester of formula 9, wherein R'=—CH=$CHCO_2Na$ and n=2, may be referred to as a cross-linked starch maleate half ester (herein sometimes referred to simply as compound 9a or as maleate 2a ) a starch half ester of formula 9, wherein R'=—$CH_2CH_2CO_2Na$ and n=2, may be referred to as a cross-linked starch succinate half ester (herein sometimes referred to simply as compound 9b or as succinate 9b); a starch half ester of formula 9, wherein R'=—CH=C($CH_3$)$CO_2Na$ or —C($CH_3$)=$CHCO_2Na$ and n=2, may be referred to as a cross-linked starch citraconate half ester (herein sometimes referred to simply as compound 9c or as citraconate 9c); a starch half ester of formula 9, wherein R'=—($CH_2$)$_3CO_2Na$ and n=2, may be referred to as a cross-linked starch glutarate half ester (herein sometimes referred to simply as compound 9d or as glutarate 9d); a starch half ester of formula 9, wherein R'=—(o—$CO_2Na$)$C_6H_4$ and n=2, may be referred to as a cross-linked starch phthalate half ester (herein sometimes referred to simply as compound 9e or as phthalate 2e); and a starch half ester of formula 9, wherein R'=—CH($SO_3Na$)$CH_2CO_2Na$, or —$CH_2$CH($SO_3Na$)$CO_2Na$, and n=2, may be referred to as a cross-linked starch sulfonate succinate half ester (herein sometimes referred to simply as compound 9f or as sulfosuccinate 9f)

Tests were conducted to compare cross-linkage of polysaccharide by activated polyethylene glycol relative to cross-linkage by divinylsulfone (DVS) of formula 10

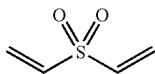

10

Comparisons were conducted on the one hand with respect to cross-linked starch compounds of formula 11a (CMS cross-linked with DVS), and 11b (starch citraconate cross-linked with DVS) and on the other hand of cross-linked starch compounds of formula 12 (CMS cross-linked with polyethylene oxide) below:

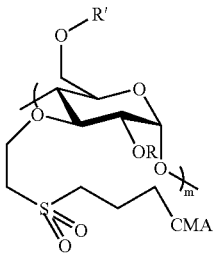

11a

R = H, half ester, crosslink
R' = carboxymethyl
m is as defined above

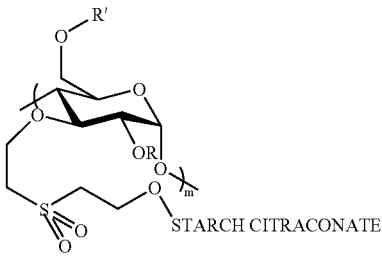

11b

STARCH CITRACONATE

R = H, half ester, crosslink
R' = —COCH=C(CH₃)CO₂Na or
—COC(CH₃)=CHCO₂Na
m is defined above

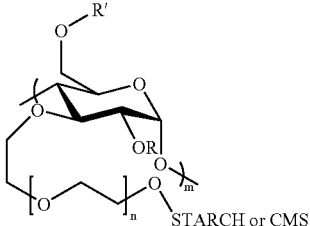

12

STARCH or CMS

R = H, carboxymethyl, crosslink
m is defined above 12a n = 1, R' = —CH₂CO₂Na (CMS)
12b n = 2, R' = —CH₂CO₂Na (CMS)
12c n = 3, R' = —CH₂CO₂Na (CMS)
12d n = 3, R' = H (STARCH)

A compound of formula 12 wherein n is 1 and R'=—CH₂CO₂Na is sometimes referred to herein simply as compound 12a; a compound of formula 12 wherein n is 2 and R'=—CH₂CO₂Na is sometimes referred to herein simply as compound 12b a compound of formula 12 wherein n is 3 and R'=—CH₂CO₂Na is sometimes referred to herein simply as compound 12c; and a compound of formula 12 wherein n is 3 and R'=H is sometimes referred to herein simply as compound 12d.

According to the Zahn-Wellens/EMPA test (US Environmental Protection Agency (EPA), Fate, Transport and Transformation Test Guidelines, OPPTS 832.3200, Zahn-Wellens/EMPA test, EPA712-C-98-084, January 1998), starch A maleate half-ester, crosslinked with triglycol dichloride 3b (herein compound 9a) having a centrifuge retention capacity (CRC) of 30 g/g in saline solution, showed 77.3%, 92.3% and 96.1% biodegradability after respectively 14, 28 and 46 days (see example 21 below).

A study of the crosslinker length was performed by preparing diglycol dichloride 3a triglycol dichloride 3b and tetraglycol dichloride 3c (SOCl₂, pyridine, dichloromethane or benzene, reflux). Experimental results thereby obtained show that carboxymethylstarch cross-linked with 0.62% of divinylsulfone 10 (namely compound of formula 11a), gives a CRC of 23 g/g in 0.9% saline solution, compared to 30 g/g when crosslinked with 9.85% of triglycol dichloride 3b (namely, compound 12b). The starch-citraconic half ester crosslinked with 0.6% of divinylsulfone 10 (namely, compound of formula 11b) were found to exhibit a good CRC (25 g/g), suggesting that carboxymethyl groups and other carboxyalkyl groups could be replaced by half esters. The effect of divinylsulfone and triglycol dichloride concentrations on the water retention of resulting compound of formula 11a, and compound 12b in 0.9% saline solution, are shown on FIG. 1. Even if 15 times more quantity of triglycol dichloride is required to reach the maximum water retention, the choice of the former is still advantageous since divinylsulfone is very expensive.

Crosslinked carboxyalkylstarches and preferably carboxymethylstarches with activated polyethylene glycols (for example the compounds 12a-12c) can be prepared in two steps. First, starch can be alkylated with halogenocarboxylates, preferably with sodium chloroacetate or other salts (Li, Ca, K, Mg) followed by crosslinking with activated polyethylene glycols. In reverse order, it is possible to perform the crosslinking before the alkylation step without negative effect on the water retention. Furthermore, these crosslinked carboxymethylstarches can also be prepared in one pot, without affecting the water retention. For alkylation and crosslinking, basic conditions are required and sodium hydroxide, potassium hydroxide, lithium hydroxide, calcium hydroxide, magnesium hydroxide, sodium or potassium carbonates, and sodium or potassium bicarbonates can be used. Sodium hydroxide is preferred.

Two example reaction schemes or process flow sheets are set forth below:

PROCESS A

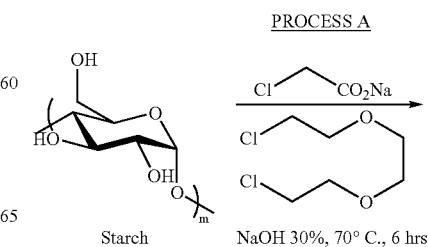

Starch     NaOH 30%, 70° C., 6 hrs

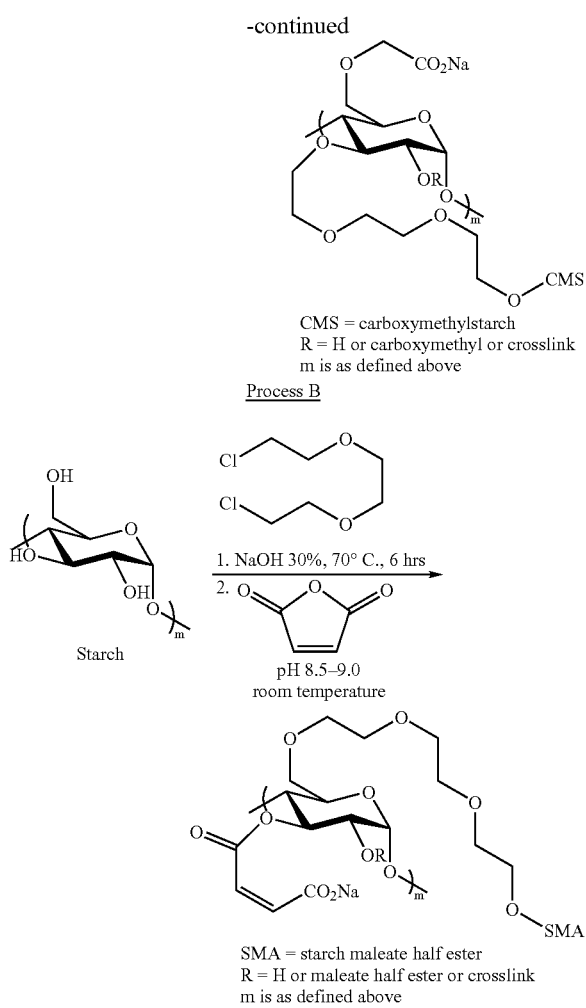

CMS = carboxymethylstarch
R = H or carboxymethyl or crosslink
m is as defined above Process B SMA = starch maleate half ester
R = H or maleate half ester or crosslink
m is as defined above Camelot Superabsorbents Limited has reported non polysaccharide-based copolymers having two or more pendant carboxylic acid groups arranged in mutual proximity to absorb water containing multivalent, particularly divalent ions (Dan and Zhong, WO 97/15367, May 1, 1997, B01D 15/00). In more specific examples, monomers having two carboxylic acid groups attached to adjacent carbon atoms are particularly preferred. In this current invention, we report the use of iminodiacetic acid disodium salt and citric acid trisodium salt as dicarboxylates and tricarboxylates pendant anionic groups to chelate divalent ions such as calcium. As a matter of fact, iminodiacetic acid disodium salt have been attached to starch to produce effective materials for heavy metal removal such as copper and cadmium (Rayford W. E. and Wing R. E., Crosslinked Cationic and Anionic Starches: Preparation and Use in Heavy Metal Removal. *Starch/Starke*, 1979, 31, 361-365; Rayford and Wing, U.S. Pat. No. 4,237,271, Dec. 2, 1980, 536/47). On the other hand, citric acid also has been attached to starch through its carboxylic acid groups for applications as ion exchanger or to enhance the dietary fibre content in foods (Wing R. E., Starch Citrate: Preparation and Ion Exchange Properties. *Starch/Starke*, 1996, 48, 275-279; Wepner et al., Citrate Starch-Application as Resistant Starch in Different Food Systems. *Starch/Starke*, 1999, 51, 354-361). In our invention, we have attached sodium citrate to starch through the secondary hydroxy group with epichlorohydrin as linker arm, leaving the tricarboxylates groups free, for calcium chelation and water absorption.

Carboxyalkyl groups attach to starch can be replaced by maleate 9a succinate 9b citraconate 9c, glutarate 9d, phthalate 9e sulfosuccinate 9f as well. Starch half esters alone, without crosslinking have been reported to be biodegradable detergent builders (Finley, U.S. Pat. No. 4,029,590, Jun. 14, 1977, 252/89R; Finley, U.S. Pat. No. 3,941,771, Mar. 2, 1976, 260/233.5) and biodegradable non-aging superabsorbers (Wolf et al., U.S. Pat. No. 6,063,914, May 16, 2000, 536/45; Buchholz et al., U.S. Pat. No. 5,789,570, Aug. 4, 1998, 536/107.). Moreover, already in 1945, Caldwell has reported an amazing increase in water absorptive powers when starch is esterified with maleic, glutaric or citraconic anhydrides (Caldwell, U.S. Pat. No. 2,461,139, Feb. 8, 1949, Cl. 260-234, application Jan. 8, 1945.).

For the preparation of starch half esters of this current invention, the crosslinking with activated polyethylene glycol is realized first at 70° C., followed by reaction with cyclic anhydrides at room temperature.

Examples of starches useful as starting materials are: corn, wheat, rice, potato, tapioca, waxy maize, sorghum, waxy sorghum, sago, and modified starches such as dextrinated, hydrolysed, oxidized, alkylated, hydroxyalkylated (in both case alkyl being for example as defined herein), acetylated, fractionated (e.g., amylose and amylopectin), and physically modified starches. Ungelatinised starches and procedure to make carboxymethylstarches without gelatinisation in organic solvents could be used. (Beenackers A. A. C. M. et al., An Experimental Study on the Carboxymethylation of Granular Potato Starch in Non-Aqueous Media, *Carbohydr. Polymers*, 2001, 45, 219-226). Other polysaccharides can also be used such as: cellulose, dextrins, polygalactomannans and more ionic and/or non-ionic derivatized, chitin/chitosan and derivatives thereof, alginate compositions, gums, xanthan gum, carageenan gum, gum karaya, gum arabic, pectin and glass-like polysaccharides (Huppéet al., WO 00/67809, Nov. 16, 2000, A61L 15/28, 15/30; Lane et al., U.S. Pat. No. 5,360,903, Nov. 1, 1994, 536/124). In general, natural polysaccharides, polysaccharides from genetically modified organisms (GMO) and synthetic polysaccharides can be used. In all cases, anionic and cationic functionalizations of the selected polysaccharide could eventually be introduced before, during or after the crosslinking.

Any other known activated polyethylene glycols may be used as cross-linkers provided that they provide a crosslinked product having the desired ether linkage as described herein. Moreover, carboxyalkyl groups attach to starch can be replaced by maleate 9a succinate 9b citraconic 9c glutaric 9d phthalates half esters 9e and sulfosuccinate 9f as well. Starch half esters alone, without crosslinking have been reported to be biodegradable detergent builders (Finley, U.S. Pat. No. 4,029,590, Jun. 14, 1977, 252/89R; Finley, U.S. Pat. No. 3,941,771, Mar. 02, 1976, 260/233.5) and biodegradable non-aging superabsorbers (Wolf et al., U.S. Pat. No. 6,063, 914, May 16, 2000, 536/45; Buchholz et al., U.S. Pat. No. 5,789,570, Aug. 4, 1998, 536/107). Moreover, already in 1945, Caldwell has reported an amazing increase in water absorptive powers when starch are esterified with maleic, glutaric or citraconic anhydrides (Caldwell, U.S. Pat. No. 2,461,139, Feb. 8, 1949, Cl. 260-234, application Jan. 8, 1945).

For the preparation of starch half esters of this current invention, the crosslinking with activated polyethylene glycol is realised first at 70° C., followed by reaction with cyclic anhydrides at room temperature.

In accordance with the present invention the presence of ionic groups (i.e. anionic or cationic groups) may enhance the absorption characteristic of a cross-linked polysaccharide.

Thus for example, the attachment of iminodicarboxylic acid disodium salt of formula 13

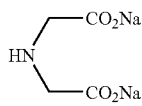

13 and citric acid trisodium salt of formula 14

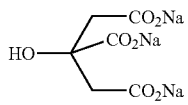

14 to starch, it is possible for example to use, as a linker arm, epichlorohydrin of formula 15

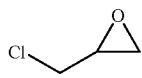

15

This linker arm showed application to attach primary, secondary and tertiary amines (Rayford W. E. and Wing R. E., Crosslinked Cationic and Anionic Starches: Preparation and Use in Heavy Metal Removal. *Starch/Starke*, 1979, 31, 361-365; Rayford and Wing, U.S. Pat. No. 4,237,271, Dec. 02, 1980, 536/47) and we have adapted the procedure for the attachment of the secondary alcohol of sodium citrate. In practice, epichlorohydrin can be attach first to starch with acid catalyst, followed by amination with iminodiactic acid disodium salt (Rayford W. E. and Wing R. E., Crosslinked Cationic and Anionic Starches: Preparation and Use in Heavy Metal Removal; *Starch/Starke*, 1979, 31, 361-365; Rayford and Wing, U.S. Pat. No. 4,237,271, Dec. 2, 1980, 536/47) or O-alkylation of sodium citrate in basic conditions. However, it has been reported that starch and epichlorohydrin appeared to form unstable adducts when hydrochloric acid catalysis was used (Trimnell D. et al. Preparation of Starch 2-Hydroxyl-3-Mercaptopropyl Ethers and Their Use in Graft Polymerizations, *J. Appl. Polymer Sc.*, 1978, 22, 3579-3586). Since perchloric acid is a better catalyst than hydrochloric acid to give higher incorporation rate of epichlorohydrin on starch, (Trimnell D. et al. Preparation of Starch 2-Hydroxyl-3-Mercaptopropyl Ethers and Their Use in Graft Polymerizations. *J. Appl. Polymer Sc.*, 1978, 22, 3579-3586) and since perchloric acid is an explosive substance, we choose an alternative approach. Since epichlorohydrin-tertiary amines adducts can be prepared first in basic condition, followed by attachment to starch in basic condition (Zhu Z. and Zhuo R., Crosslinked Quaternary Ammonium Cornstarch Matrix for Slow Release of Carboxylic Groups-containing Herbicides. *Starch/Starke*, 2000, 52, 58-63; EDANA, Recommended Test Method: Centrifuge Retention Capacity in Saline by Gravimetric Determination 441.1-99, February, 1999), we have selected this alternative procedure for the attachment of iminodiacetic acid disodium salt and citric acid trisodium salt on starch.

It is to be understood herein, that if a "range" or "group of substances", "group of substituents or functional groups" or the like is mentioned or if ranges of other types of a particular characteristic (e.g. temperature, pressure, chemical structure, concentration, molecular weight, time, etc.) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a time range, temperature range, a pressure range, a pH range etc., this is to be understood as specifically incorporating herein each and every individual time, temperature, pressure, and pH state etc., as well as sub-ranges thereof; i.e. a temperature above 100° C., is to be understood as specifically referring to 101° C., 105° C. and up, 110° C. and up, 115° C. and up, 110 to 135° C., 115° C. to 135° C., 102° C. to 150° C., up to 210° C., etc.; and with respect to a class or group of substituents or functional groups, this is to be understood as specifically incorporating herein each and every individual member of the class or group as well as sub-classes or sub-groups thereof, i.e. a reference to alkyl of 1 to 5 carbon atoms is to be understood as specifically referring to each and every individual alkyl group (e.g. methyl, propyl, butyl, etc.) as well as to subgroups such as 2 to 5 carbon atoms, 1 to 3 carbon atoms, 2 to 4 carbon atoms etc.; and similarly with respect to other parameters such as, concentrations, molecular weights, etc.

Figure 2:
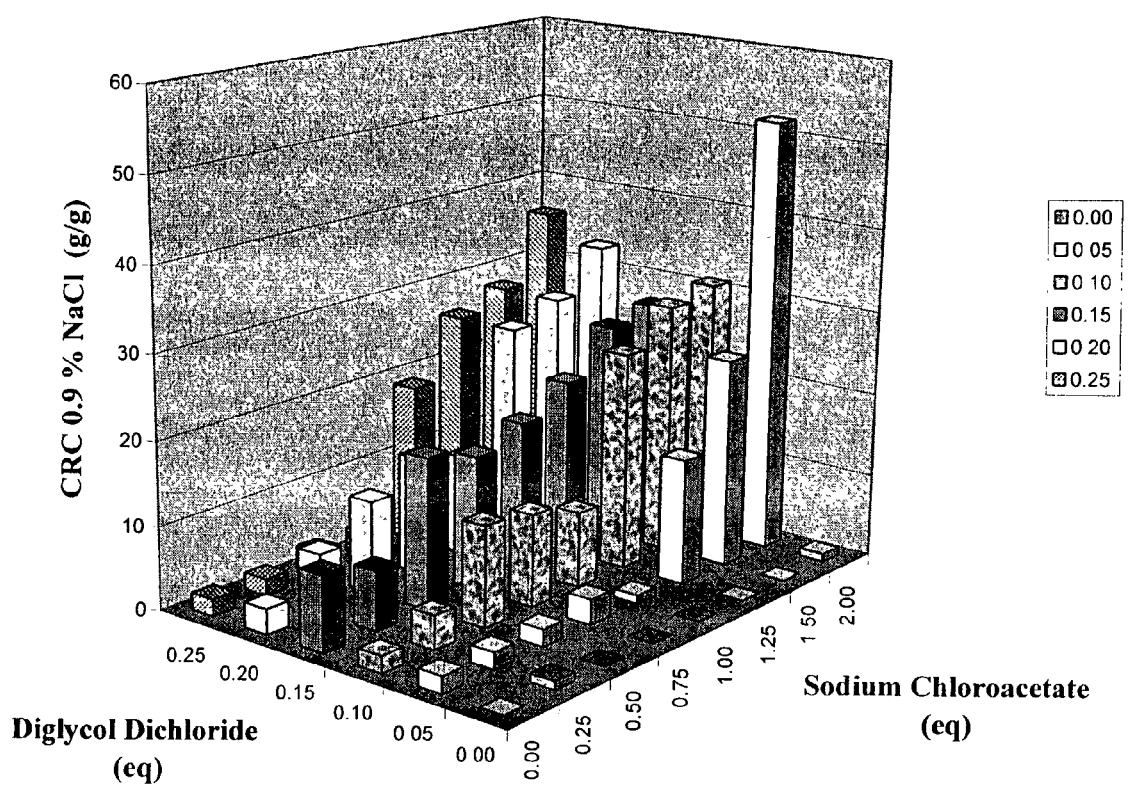
Figure 3:
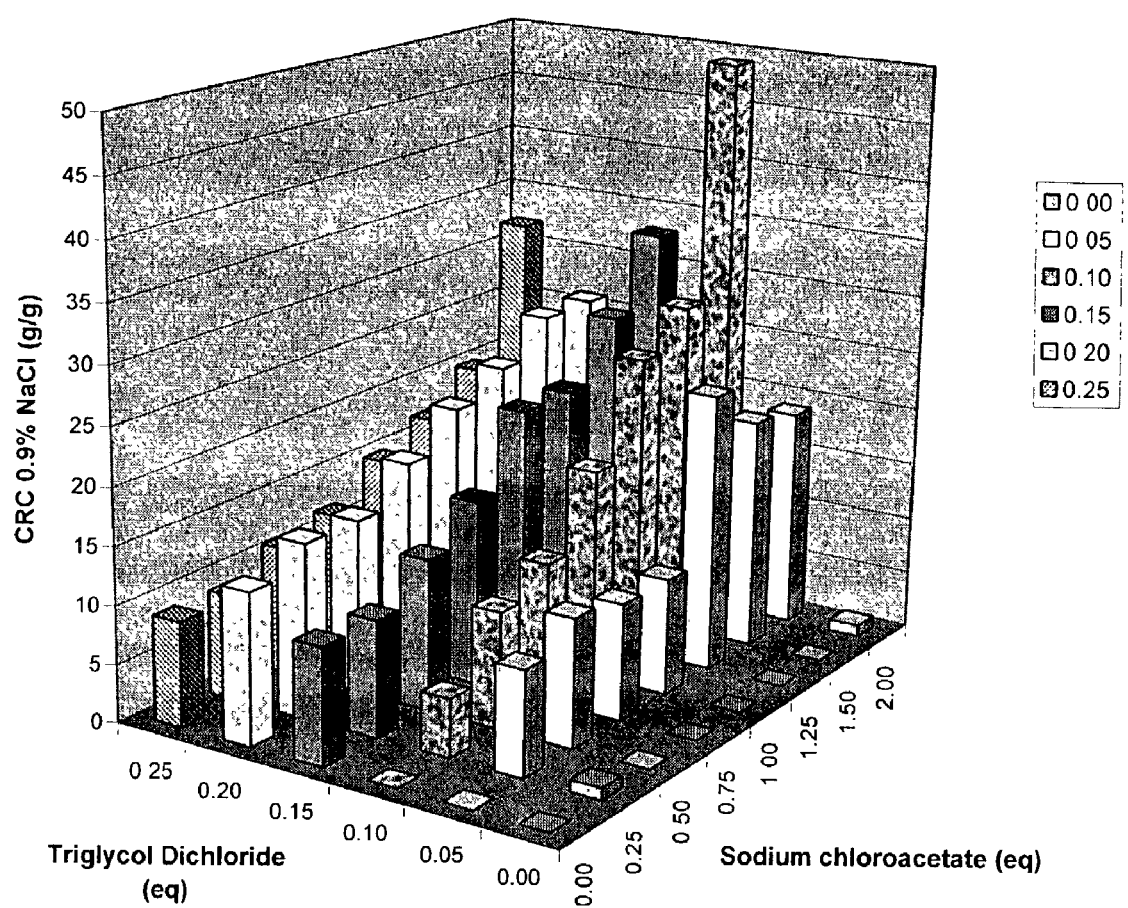
Figure 4:
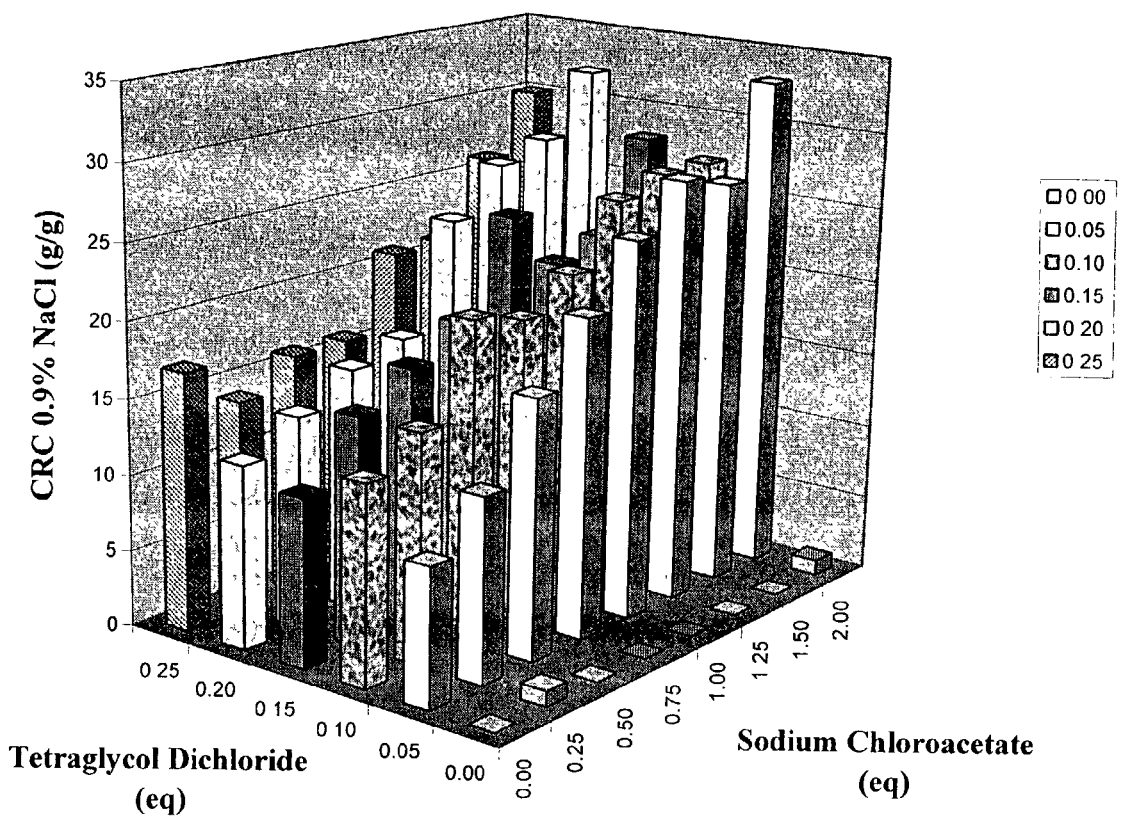
Figure 5:
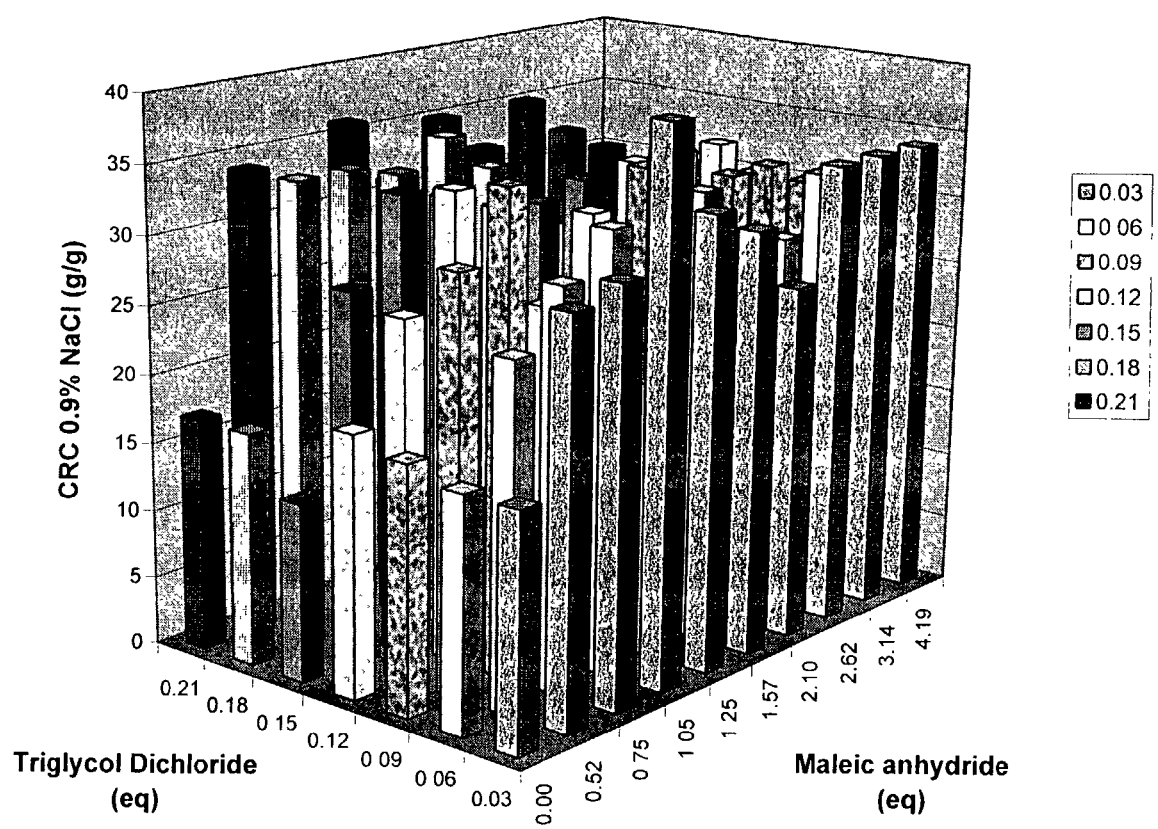

In the drawings which illustrate example embodiments of the present invention:

FIG. 1: Effect of triglycol dichloride ($T_3G$—diCl) and divinyl sulfone (DVS) concentrations on crosslinked carboxymethylstarch' CRC;

FIG. 2: Effect of sodium chloroacetate (SCA) and diglycol dichloride (DG—diCl) concentrations on starch derivatives' CRC;

FIG. 3: Effect of sodium chloroacetate (SCA) and triglycol dichloride ($T_3G$—diCl) concentrations on starch derivatives' CRC;

FIG. 4: Effect of sodium chloroacetate (SCA) and tetraglycol dichloride ($T_4G$—diCl) concentrations on starch derivatives' CRC;

FIG. 5: Effect of maleic anhydride (MA) and triglycol dichloride ($T_3G$—diCl) concentrations on starch derivatives' CRC—Optimization study; and FIG. 6: Effect of maleic anhydride (MA) and triglycol dichloride ($T_3G$—diCl) concentrations on starch derivatives' CRC—Optimization study.

CENTRIFUGE RETENTION CAPACITY (CRC)

The centrifuge retention capacity (CRC) has been measured by the following procedure which represents a modified procedure from the EDANA test method (EDANA, Recommended Test Method: Centrifuge Retention Capacity in Saline by Gravimetric Determination 441.1-99, February, 1999) and a modified procedure described by Annergren and Lundstrom (Annergren and Lundstrom. WO 00/21581, Apr. 20, 2000, A61L 15/28, 15/60.).

Two empty 15 ml test tubes (duplicata) are weighted ($T_e$). Samples around 0.3 g±0.005 g (S) are introduced into both tubes. Saline solution (0.9%, 10 ml) is added and the gel is vortexed for 1 minute then allowed to stand for 15 minutes. Tubes are centrifuged at 2000 RPM for 5 minutes and the upper aqueous layer is decanted at 30° angle for 5 seconds and tubes are weighted again ($T_s$). In case there is no aqueous layer, the procedure is repeated with 0.2 g±0.005 g samples. CRC is calculated according to the equation (1) and is expressed in g of saline solution per g of absorbent.

$$CRC = \frac{Ts - Te - S}{S} \quad (1)$$

Those skilled in the art will gain further and better understanding of this invention and the new and important advantages, which is offered from the following illustrative, but not limiting, examples of this invention as it has been carried out.

Gel Strength

The gel strength is arbitrary measured on a 0 to 5 scale, where 0=no gel, (liquid), 1=viscous liquid, 2=soft gel, 3=medium gel, 4=hard gel, and 5=very hard gel.

Biodegradability

According to the U.S. Environmental Protection Agency (EPA), the Zahn-Wellens test is useful to test the biodegradability of a substance soluble in water to at least 50 mg of dissolved organic carbon (DOC) per litre (U.S. Environmental Protection Agency (EPA), Fate, Transport and Transformation Test Guidelines, OPPTS 832.3200, Zahn-Wellens/EMPA test, EPA712-C-98-084, January 1998). For substances which are not completely soluble it offers only a qualitative indication of whether these substances are basically susceptible to biological degradation or not (Buchholz et al., U.S. Pat. No. 5,789,570, Aug. 4, 1998, 536/107).

We used activated sludge to evaluate the biodegradability of compound 9a (example 21). Technicon carbon analyser has been used to measure DOC and the percentage of biodegradability has been calculated according to DOC obtained and reported in the equation given in reference 36. Compound 9a showed no toxicity for microorganisms and no toxic product have been detected to destroy the aquatic flora, particularly the micro crustacean: *Daphnia magna*. The blank used was the mineral medium alone and the positive control was ethylene glycol, which showed 100% biodegradability after 14 days.

Preparation of Crosslinkers

EXAMPLE 1

Preparation of the 1,5-dichloro-3-oxapentane (Diglycol Dichloride 3a)

10.0 g (94 mmol) of diethylene glycol were dissolved in 100 ml benzene. To this solution, 30.8 ml (4 eq.) of pyridine were added, followed by a dropwise addition of 27.5 ml (4 eq.) of thionylchloride. The reaction mixture was heated at reflux for 24 hours. At room temperature, the organic layer was decanted from the pyridinium hydrochloride salt, washed with 150 ml of water, dried on anhydrous sodium sulfate, filtered and evaporated to dryness to give 8.4 g (65% yield) of the dichloride as a light yellow liquid, used without further purification. Infrared spectroscopy showed the absence of hydroxyl band.

IR (neat): 2964, 2865, 1450, 1125, 747, 669 $cm^{-1}$.

EXAMPLE 2

Preparation of 1,8-dichloro-3,6-dioxaoctane (Triglycol Dichloride 3b)

10.0 g (67 mmol) of triethylene glycol were treated as example 1 with 22 ml (4 eq.) of pyridine and 19 ml (4 eq.) of thionylchloride to give 8.8 g (62% yield) of the dichloride as a yellow oil, used without further purification. Infrared spectroscopy showed the absence of hydroxyl band.

IR (neat): 2962, 2870, 1452, 1123, 747, 666 $cm^{-1}$.

EXAMPLE 3

Preparation of 1,11-dichloro-3,6,9-trioxaundecane (Tetraglycol Dichloride 3c)

10.0 g (52 mmol) of tetraethylene glycol were treated as example 1 with 17 ml (4 eq. ) of pyridine and 15 ml (4 eq.) of thionylchloride to give 7.2 g (61% yield) of the dichloride as a yellow oil, used without further purification. Infrared spectroscopy showed the absence of hydroxyl band.

IR(neat): 2951, 2870, 1459, 1118, 746, 665 $cm^{-1}$.

Comparaison of Divinylsulfone and Triglycol Dichloride as Crosslinkers to Obtain Starch-based Superabsorbents (FIGS. 1, 2)

EXAMPLE 4

Preparation of a Carboxymethylstarch, Crosslinked with 0.62% w/w Divinylsulfone: Compound 11a 2.0 g (12.3 mmol) of wheat starch A (Supercell 1201-C, ADM/Ogilvie) was suspended in 40 ml of deionized water. Under stirring, 3.5 ml 30% NaOH (26.3 mmol, 2.1eq.) was added dropwise and the solution stirred at room temperature for 1 hour. Chloroacetic acid (1.16 g, 12.3 mmol, 1 eq), dissolved in 10 ml of deionized water and neutralized with 1.6 ml 30% NaOH (12.3 mmol, 1 eq.) was added dropwise and the reaction mixture was heated at 70° C. for 24 hours. At room temperature, 12 mg (0.62 weight %) of divinylsulfone dissolved in 10 ml acetone, was added dropwise and the solution was stirred for 2 hours. The polymer was precipitated with 100 ml of methanol, triturated in a blender, washed with 3 portions of 60 ml methanol, filtered and dry at 60° C. for 16 hours to give 1.97 g of a white solid. The solid was grinded with a coffee grinder to get compound 11a as a fine powder.

IR (KBr): 3428, 2928, 1611, 1430, 1159, 1083, 1020, 762, 711, 577 $cm^{-1}$.

CRC=23 g/g

EXAMPLE5

Preparation of a Carboxymethylstarch, Crosslinked with 39.38% w/w Divinylsulfone: Compound 11a 2.0 g of wheat starch A was treated as in example 4 with 0.784 g (39.38 weight %) of divinylsulfone dissolved in 10 ml acetone to give 2.35 g of compound 11a as a fine white powder.

EXAMPLE 6

Preparation of Carboxymethylstarch, Crosslinked with 9.85% w/w Triglycol Dichloride: Compound 12b 2.0 g (12.3 mmol) of wheat starch A (Supercell 1201-C, ADM/Ogilvie) was suspended in 40 ml of deionized water. Under stirring, 3.5 ml 30% NaOH (26.3 mmol, 2.1 eq.) was added dropwise and the solution stirred at room temperature for 1 hour. Chloroacetic acid (1.16 g, 12.3 mmol, 1.0 eq), dissolved in 10 ml of deionized water and neutralized with 1.6 ml 30% NaOH (12.3 mmol, 1.0 eq.) was added dropwise and the reaction mixture was heated at 70° C. for 24 hours. At room temperature, 0.197 g (9.85 weight %) of triglycol dichloride dissolved in 10ml acetone, was added dropwise and the solution was heated at 70° C. for 24 hours. The polymer was precipitated with 100 ml of methanol, triturated in a blender, washed with 3 portions of 60 ml methanol, filtered and dry at 60° C. for 16 hours to give 1.95 g of a white solid. The solid was grinded with a coffee grinder to get compound 12b as fine powder.

IR(KBr): 3408, 2929, 1607, 1423, 1327, 1158, 1083, 1021, 937, 849, 762, 710, 581, 530 cm$^{-1}$.

CRC=0 g/g

EXAMPLE 7

Preparation of Carboxymethylstarch, Crosslinked with 40% w/w Triglycol Dichloride: Compound 12b 2.0 g of wheat starch A was treated as in example 6 with 0.80 g (40 weight %) of triglycol dichloride dissolved in 10 ml acetone to give 2.06 g of compound 12b as a fine white powder.

IR (KBr): 3404, 2928, 1607, 1424, 1327, 1155, 1084, 1020, 934, 849, 762, 710, 580, 530 cm$^{-1}$.

CRC=21 g/g

The CRC results for the materials of examples 6 and 7, as well as for other starting concentrations are shown in table II and FIG. 1, below, table II appearing after the examples below.

Referring to FIG. 1, this figure illustrates the "Effect of triglycol dichloride (T$_3$G—diCl) and divinyl sulfone (DVS) concentrations on crosslinked carboxymethylstarch' CRC". The FIG. 1 shows that for the crosslinking of carboxymethylstarch (1.0 eq sodium chloroacetate used), the optimum concentration of divinylsulfone is reached at lower concentration than triglycol dichloride. A concentration of 0.62% of divinylsulfone gives a CRC of 23 g/g and a concentration of 9.85% of triglycol dichloride gives a CRC of 30 g/g. Therefore, triglycol dichloride is superior to divinylsulfone as crosslinker for carboxymethylstarch to obtain high CRC. The figure also shows that at low concentration of triglycol dichloride (0 to 5% weight), no gel is obtained and a concentration as low as 0.31% weight of divinylsulfone is sufficient to obtain a gel.

Effect of Sodium Chloroacetate Concentration, Crosslinker Length and Crosslinker Concentration on CRC (FIGS. 2-4)

EXAMPLE 8

Preparation of Carboxymethylstarch, with 0.25 Eq Sodium Chloroacetate and without Crosslinkage 2.0 g (12.3 mmol) of wheat starch A (Supercell 1201-C, ADM/Ogilvie) was suspended in 40 ml of deionized water. Under stirring at 2000 rpm, 5.0 ml 30% NaOH (37 mmol, 3.0 eq.) was added dropwise and the solution stirred at room temperature for 1 hour. Sodium chloroacetate (1.13ml, 2.74 M, 3.10 mmol, 0.25 eq) was added dropwise and the reaction mixture was heated at 70° C. for 16 hours. The polymer was precipitated with 75 ml of methanol, and the mother liquor is discarded. The polymer is triturated in a blender with 150 ml methanol, filtered, washed with 3 portions of 50 ml methanol, and dry at 60° C. for 16 hours to give carboxymethylstarch as a fine white powder after grinding.

CRC=1 g/g

Gel Strength (GS)=0

EXAMPLE 9

Preparation of Carboxymethylstarch with 2.0 Eq. Sodium Chloroacetate and Crosslinked with 0.05 Eq. Diglycol Dichloride: Compound 12a 2.0 g (12.3 mmol) of wheat starch A (Supercell 1201-C, ADM/Ogilvie) was suspended in 40 ml of deionized water. Under stirring at 2000 rpm, 5.0 ml 30% NaOH (37 mmol, 3.0 eq.) was added dropwise and the solution stirred at room temperature for 1 hour. Sodium chloroacetate (9.0 ml, 2.74 M, 24.7 mmol, 2.0 eq) was added dropwise followed by diglycol dichloride (88 mg, 6.17 mmol, 0.05 eq.), weighted in 1.0 ml seringue, and the reaction mixture was heated at 70° C. for 16 hours. The polymer was treated as in example 9 to give compound 12a as a fine powder.

CRC=52 g/g

Gel strength(GS)=2

EXAMPLE 10

Preparation of Carboxymethylstarch with 0.5Eq. Sodium Chloroacetate and Crosslinked with 0.20Eq. Diglycol Dichloride: Compound 12a 2.0 g (12.3 mmol) of wheat starch A was treated as in example 9 with sodium chloroacetate (2.26 ml, 2.74 M, 6.17 mmol, 0.5 eq) and diglycol dichloride (353 mg, 2.47 mmol, 0.20 eq.) to give compound 12a as a fine powder.

CRC=11 g/g

Gel strength (GS)=4

EXAMPLE 11

Preparation of Carboxymethylstarch with 2.0 Eq. Sodium Chloroacetate and Crosslinked with 0.20 Eq. Diglycol Dichloride: Compound 12a 2.0 g (12.3 mmol) of wheat starch A was treated as in example 9 with sodium chloroacetate (9.0 ml, 2.74 M, 24.7 mmol, 2.0 eq.) and diglycol dichloride (353 mg, 2.47 mmol, 0.20 eq.) to give compound 12a as a fine powder.

CRC=33 g/g

Gel strength (GS)=4

The CRC and gel strength results for the materials of examples 8 to 11, as well as for other starting concentrations are shown in table III and FIG. 2, below, table III appearing after the examples below.

Referring to FIG. 2, this figure illustrates the effect of sodium chloroacetate (SCA) and diglycol dichloride (DG—diCl) concentrations on starch derivatives' CRC. The FIG. 2 (and table III) show that no gel are obtained when no crosslinker (diglycol dichloride) is used. When only the crosslinker is attached to starch in the absence of sodium chloroacetate, a viscous liquid absorbent (CRC of 9 g/g and GS of 1 from table III) can be obtained (0.15 eq diglycol dichloride, no sodium chloroacetate). The figure also shows the concentration region when it is possible to obtain superabsorbency (CRC greater than 15 g/g in saline solution) with a CRC maximum of 52 g/g, when 0.05 eq of diglycol dichloride and 2.00 eq of sodium chloroacetate are used. For this experiment, only a soft gel is obtained (GS of 2 from table III). According to table III, hard gels are especially obtained when 0.20 eq of diglycol dichloride, independently of the sodium chloroacetate concentration used. The best result obtained with diglycol dichoride in term of CRC and GS has been found to be respectively 36 g/g and 5, when 0.25 eq of diglycol dichloride and 2.0 eq of sodium chloroacetate are used.

EXAMPLE 12

Preparation of Carboxymethylstarch with 0.5 Eq. Sodium Chloroacetate and Crosslinked with 0.05 Eq. Triglycol Dichloride: Compound 12b 2.0 g (12.3 mmol) of wheat starch A was treated as in example 9 with sodium chloroacetate (2.3 ml, 2.74 M, 6.17 mmol, 0.5 eq.) and triglycolglycol dichloride (115 mg, 0.62 mmol, 0.05 eq.) to give compound 12b as a fine powder.

CRC=11 g/g

Gel strength (GS)=2

EXAMPLE 13

Preparation of Carboxymethylstarch with 2.0 Eq. Sodium Chloroacetate and Crosslinked with 0.10 Eq. Triglycol Dichloride: Compound 12b 2.0 g (12.3 mmol) of wheat starch A was treated as in example 9 with sodium chloroacetate (9.0 ml, 2.74 M, 24.7 mmol, 2.0 eq.) and triglycolglycol dichloride (115 mg, 0.062 mmol, 0.05 eq.) to give compound 12b as a fine powder.

CRC=49 g/g

Gel strength (GS)=3

EXAMPLE 14

Preparation of Carboxymethylstarch with 1.5 Eq. Sodium Chloroacetate and Crosslinked with 0.15 eq. Triglycol Dichloride; Compound 12b 2.0 g (12.3 mmol) of wheat starch A was treated as in example 9 with sodium chloroacetate (6.8 ml, 2.74 M, 18.5 mmol, 1.5 eq.) and triglycolglycol dichloride (346 mg, 1.85 mmol, 0.15 eq.) to give compound 12b as a fine powder.

CRC=27 g/g

Gel strength (GS)=5

EXAMPLE 15

Preparation of Carboxymethylstarch with 0.25 Eq. Sodium Chloroacetate and Crosslinked with 0.20 Eq. Triglycol Dichloride; Compound 12b 2.0 g (12.3 mmol) of wheat starch A was treated as in example 9 with sodium chloroacetate (1.1 ml, 2.74 M, 3.09 mmol, 0.25 eq.) and triglycolglycol dichloride (462mg, 2.47 mmol, 0.20 eq.) to give compound 12b as a fine powder.

CRC=15 g/g

Gel strength (GS)=2

The effect of sodium chloroacetate (SCA) and triglycol dichloride ($T_3G$—diCl) concentrations on starch derivatives' CRC for the materials of examples 12 to 15, as well as for other starting concentrations are shown in table IV and FIG. 3, below, table IV appearing after the examples below.

Referring to FIG. 3, this figure illustrates the dffect of sodium chloroacetate (SCA) and triglycol dichloride ($T_3G$—diCl) concentrations on starch derivatives' CRC. The FIG. 3 (and table IV) shows that a medium gel or hard gel absorbent are obtained when the crosslinker (triglycol dichloride) is used, without sodium chloroacetate. More specifically, 0.15 eq of triglycol dichloride gives a hard gel absorbent with a CRC of 10 g/g. The figure also shows the concentration region for superabsorbency (CRC higher than 15 g/g in saline solution) with a CRC maximum of 49 g/g, when 0.10 eq of diglycol dichloride and 2.00 eq of sodium chloroacetate are used. For this experiment, a medium gel is obtained (GS of 3 from table IV). According to table IV, very hard gels are obtained when 0.15 eq of triglycol dichloride are used, with sodium chloroacetate concentration varying from 1.0 eq to 1.5 eq and with 0.20 eq. of triglycol dichloride with 2.0 eq. of sodium chloroacetate. For very hard gels, the optimum is reached at a CRC of 27 g/g (0.20 eq. triglycol dichloride and 2.0 eq sodium chloroacetate).

EXAMPLE 16

Preparation of Carboxymethylstarch with 0.50 eq. Sodium Chloroacetate and Crosslinked with 0.05 eq. Tetraglycol Dichloride: Compound 12c 2.0 g (12.3 mmol) of wheat starch A was treated as in example 9 with sodium chloroacetate (2.3 ml, 2.74 M, 6.17 mmol, 0.50 eq.) and tetraglycolglycol dichloride (143 mg, 0.617 mmol, 0.05 eq.) to give compound 12c as a fine powder.

CRC=17 g/g

Gel strength (GS)=5

EXAMPLE 17

Preparation of Carboxymethylstarch with 2.0 Eq. Sodium Chloroacetate and Crosslinked with 0.05 Eq. Tetraglycol Dichloride: Compound 12c 2.0 g (12.3 mmol) of wheat starch A was treated as in example 9 with sodium chloroacetate (9.0 ml, 2.74 M, 24.7 mmol, 2.0 eq.) and tetraglycolglycol dichloride (143 mg, 0.617 mmol, 0.05 eq.) to give compound 12c as a fine powder.
CRC=33 g/g
Gel strength (GS)=5

EXAMPLE 18

Preparation of carboxymethylstarch with 1.0 eq. sodium chloroacetate and crosslinked with 0.15 eq. tetraglycol dichloride: compound 12c 2.0 g (12.3 mmol) of wheat starch A was treated as in example 9 with sodium chloroacetate (4.5 ml, 2.74 M, 12.3 mmol, 1.0 eq.) and tetraglycolglycol dichloride (428 mg, 1.85 mmol, 0.15 eq.) to give compound 12c as a fine powder.
CRC=25 g/g
Gel strength (GS)=3

EXAMPLE 19

Preparation of Starch Crosslinked with 0.25 eq. Tetraglycol Dichloride: Compound 12d 2.0 g (12.3 mmol) of wheat starch A was treated as in example 9 except that sodium chloroacetate was omitted and tetraglycol dichloride (713 mg, 3.09 mmol, 0.25 eq.) was used to give compound 12d as a fine powder.
CRC=17 g/g
Gel strength (GS)=3

The effect of sodium chloroacetate (SCA) and triglycol dichloride ($T_3G$—diCl) concentrations on starch derivatives' CRC for the materials of examples 16 to 19, as well as for other starting concentrations are shown in table IV and FIG. 3, below, table IV appearing after the examples below.

Referring to FIG. 4, this figure illustrates the effect of sodium chloroacetate (SCA) and tetraglycol dichloride ($T_4G$—diCl) concentrations on starch derivatives' CRC. The FIG. 4 (and table V) shows that a medium gel superabsorbents is obtained when the crosslinker (tetraglycol dichloride) is used, without sodium chloroacetate. More specifically, 0.25 eq of tetraglycol dichloride gives a medium gel superabsorbent with a CRC of 17 g/g. The figure also shows the concentration region where superabsorbency (CRC higher than 15 g/g) is obtained with a CRC maximum of 33 g/g, when 0.05 eq of tetraglycol dichloride and 2.0 eq of sodium chloroacetate are used. For this experiment, a very hard gel is obtained (GS of 5 from table V). According to table V, very hard gels are frequently obtained with tetraglycol dichloride by comparison to other crosslinkers (tables III and IV). For very hard gels, the optimum is reached at a CRC of 27 g/g (0.15 eq. Triglycol dichloride and 1.5 eq sodium chloroacetate).

Other Carboxylate Groups

EXAMPLE 20

Preparation of Starch Citraconate Half Ester, Crosslinked with 0.62% w/w Divinylsulfone: Compound 11b 2.0 g (12.3 mmol) of wheat starch A (Supercell 1201-C, ADM/Ogilvie) was suspended in 40 ml of deionized water. Under stirring, 5.0 ml 30% NaOH (37.5 mmol, 3 eq.) was added dropwise and the solution stirred at room temperature for 1 hour. Citraconic anhydride (1.73 g, 13.3 mmol, 1.1 eq.), dissolved in 10 ml acetone was added dropwise and the reaction mixture was stirred at room temperature for 2 hours. 12 mg (0.62%) of divinylsulfone, dissolved in 10 ml acetone, was added dropwise and the solution was stirred for 2 hours. The polymer was treated as in example 4 to give 1.92 g of compound 11b as a fine white powder.
IR (KBr): 3399, 2929, 1715, 1644, 1571, 1446, 1407, 1276, 1153, 1081, 1026, 930, 853, 762, 710, 579, 530 cm⁻.
CRC=25 g/g
Gel strength (GS)=5

EXAMPLE 21

Preparation of Starch Maleate Half Ester, Crosslinked with 0.08 Eq. Triglycol Dichloride: Compound 9a 6.0 g (37.1 mmol) of wheat starch A (Supercell 1201-C, ADM/Ogilvie) was suspended in 120 ml of deionized water. Under stirring, 2.5 ml 30% NaOH (18.6 mmol, 0.5 eq.) was added dropwise and the solution stirred at room temperature for 1 hour. Triglycol dichloride (0.5 ml, 2.97 mmol, 0.08eq.) was added and the solution was heated at 70° C. for 16 hours. After cooling at room temperature, maleic anhydride (18 ml, 1.64 M in ethyl acetate, 29.6 mmol, 0.8eq.) was added and the two phases mixture was vigorously stirred at room temperature for 1 hour. The polymer was precipitated with 225 ml of methanol, and the mother liquor is discarded. The polymer is triturated in a blender with 450 ml methanol, filtered, washed with 3 portions of 150 ml methanol, and dry at 60° C. for 16 hours to give after grinding, 6.58 g of compound 9a as a fine white powder.
IR (KBr): 3398, 2931, 1720, 1632, 1583, 1423, 1351, 1304, 1228, 1155, 1081, 1024, 934, 850, 762, 709, 610, 578, 530 cm⁻¹.
CRC=33 g/g
Gel strength (GS)=5
Biodegradability: 77.3, 92.3 and 96.1% after 14, 28 and 46 days, respectively.

EXAMPLE 22

Preparation of Disodium Iminodicarboxylate Epichlorohydrin Adduct 16

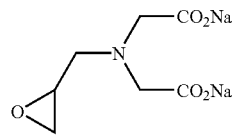

Iminodiactic acid (3.28 g, 24.6 mmol) was dissolved in 6.6 ml 30% NaOH (2.0 eq.) and epichlorohydrin (1.92 ml, 24.6 mmol) was added. The heterogeneous reaction mixture was stirred at room temperature for 2 hours to give an homogeneous solution which was completed to 20 ml with deionized water. Samples of this stock solution were used without further purification. Since the reaction has been done with a strong base (NaOH), we expect the presence of the epoxide group instead of the N-(3-chloro-2-hydroxypropyl) group, as reported by Zhu and Zhuo (Zhu Z. and Zhuo R., Crosslinked Quaternary Ammonium Cornstarch Matrix for Slow Release of Carboxylic Groups-containing Herbicides. *Starch/Starke*, 2000, 52, 58-63.) for a reaction between epichlorohydrin and trimethylamine at pH 9.1.

EXAMPLE 23

Preparation of Trisodium Citrate Epichlorohydrin Adduct 17

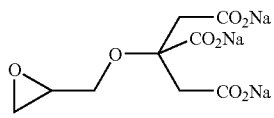

17

Trisodium citrate (7.23 g, 24.6 mmol) was dissolved in 3.3 ml 30% NaOH (1.0 eq.) and epichlorohydrin (1.92 ml, 24.6 mmol) was added. The heterogeneous reaction mixture was stirred at room temperature for 16 hours to give an homogeneous solution which was completed to 20 ml with deionized water. Samples of this stock solution were used without further purification. For the same reason discussed in example 22, we expect the presence of the epoxide group in the adduct.

EXAMPLE 24

Preparation of Starch Dicarboxylates of Formula 18a

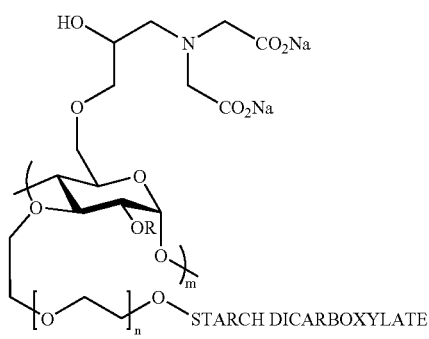

18a

R=H, dicarboxylate, crosslink n=2 m is as defined above 2.0 g (12.3 mmol) of wheat starch A was suspended in 40 ml of deionized water. Under stirring, 3.3 ml 30% NaOH (24.3 mmol, 2.0eq.) was added dropwise and the solution stirred at room temperature for 1 hour. The disodium iminidiacetate epichlorohydrin adduct solution (15.0 ml 18.45 mmol, 1.5 eq), was added dropwise, followed by triglycol dichloride (0.30 ml, 1.85 mmol, 0.15 eq.) and the reaction mixture was heated at 70° C. for 24 hours. The polymer was treated as in example 9 to give compound 18a as a fine powder.

IR (KBr): 3408, 2929, 1607, 1423, 1327, 1158, 1083, 1021, 937, 849, 762, 710, 581, 530 cm$^{-1}$.

CRC=24 g/g

Gel strength (GS)=4

EXAMPLE 25

Preparation of Starch Tricarboxylates of Formula 19a

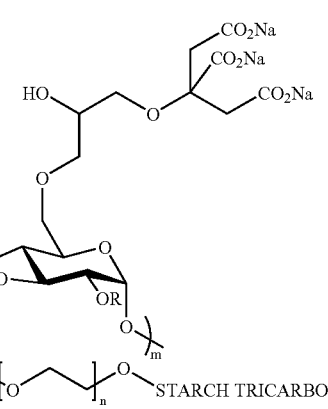

19a

R=H, tricarboxylate, crosslink n=2 m is as defined above 2.0 g (12.3 mmol) of wheat starch A was suspended in 40 ml of deionized water. Under stirring, 3.3 ml 30% NaOH (24.3 mmol, 2.0 eq.) was added dropwise and the solution stirred at room temperature for 1 hour. The trisodium citrate epichlorohydrin adduct solution (15.0 ml 18.45 mmol, 1.5 eq), was added dropwise, followed by triglycol dichloride (0.30 ml, 1.85 mmol, 0.15 eq.) and the reaction mixture was heated at 70° C. for 24 hours. The polymer was treated as in example 9 to give compound 19a as a fine powder.

IR(KBr): 3408, 2929, 1607, 1423, 1327, 1158, 1083, 1021, 937, 849, 762, 710, 581, 530 cm$^{-1}$.

CRC=23 g/g

Gel strength (GS)=4

Figure 6:
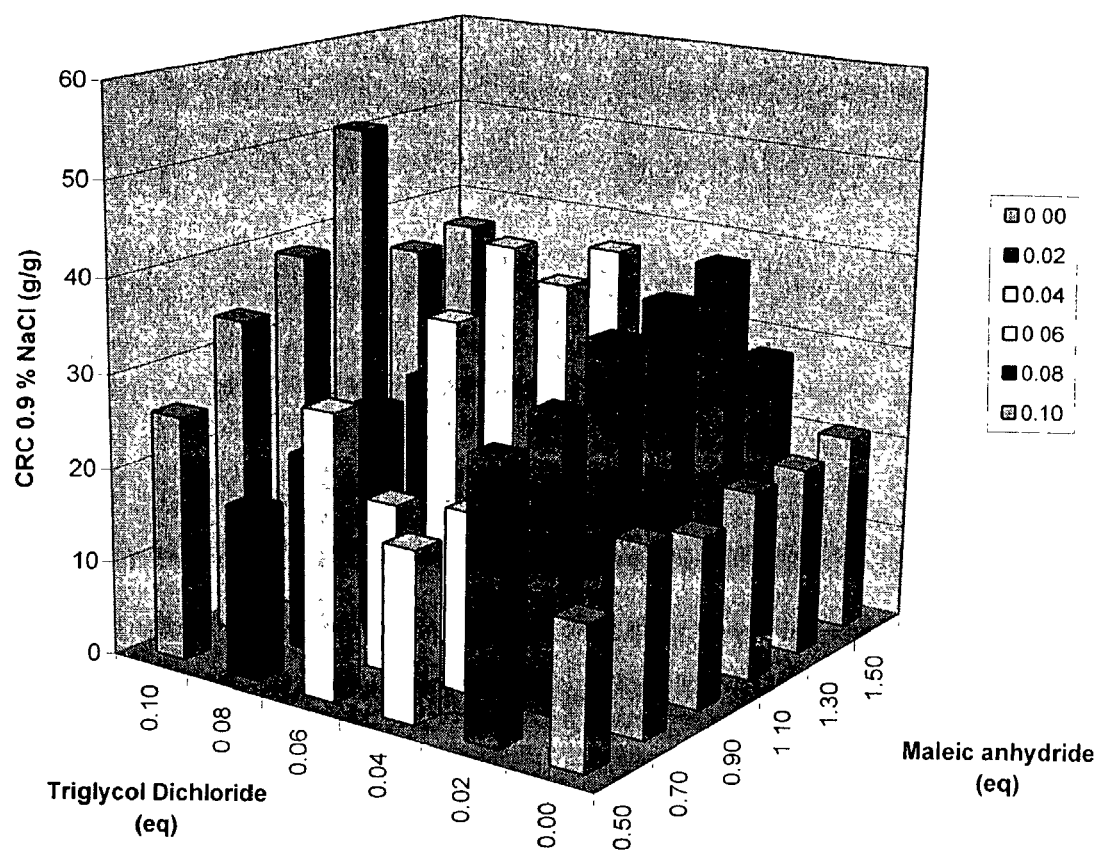

Centrifugal Retention Capacity and Gel Strength Optimization for Starch Maleate Half Ester, Crosslinked with Triglycol Dichloride, Compound 9a, (FIGS. 5 and 6)

EXAMPLE 26

Preparation of Starch Crosslinked with 0.03 Eq. Triglycol Dichloride, Compound 12d 2.0 g (12.3 mmol) of wheat starch A (Supercell 1201-C, ADM/Ogilvie) was suspended in 40 ml of deionized water. Under stirring, 0.82 ml 30% NaOH (6.17 mmol, 0.50 eq.) was added dropwise and the solution stirred at room temperature for 1 hour. Triglycol dichloride (0.5 ml, 2.97 mmol, 0.08 eq.) was added and the solution was heated at 70° C. for 16 hours. After cooling at room temperature, the pH was adjusted between 8.5 and 9.0 and the polymer was precipitated with 150 ml of methanol, and the mother liquor is discarded. The polymer is triturated in a blender with 150 ml methanol, filtered, washed with 2 portions of 50 ml methanol, and dry at 60° C. for 16 hours to give after grinding, compound 12d as a fine white powder.

IR(KBr): 3387, 2927, 2891, 1641, 1464, 1432, 1370, 1156, 1081, 1023, 930, 850, 762, 711 and 680 cm$^{-1}$.

CRC=17 g/g

Gel strength (GS)=4

EXAMPLE 27

Preparation of Starch Maleate Half Ester with 1,05 Eq. Maleic Anhydride, and Crosslinked with 0.03 Eq. Triglycol Dichloride, Compound 9a 2.0 g (12.3 mmol) of wheat starch A (Supercell 1201-C, ADM/Ogilvie) was suspended in 40 ml of deionized water. Under stirring, 0.82 ml 30% NaOH (6.17 mmol, 0.50 eq.) was added dropwise and the solution stirred at room temperature for 1 hour. Triglycol dichloride (69 mg, 0.37 mmol, 0.03 eq.) was added and the solution was heated at 70° C. for 16 hours. After cooling at room temperature, the pH was adjusted between 8.5 to 9.0 and maleic anhydride (8.9 ml, 1.45 M in ethyl acetate, 13.0 mmol, 1.05 eq.) was slowly added and the aqueous mixture containing ethyl acetate droplets was vigorously stirred at 300 RPM at room temperature. During the addition, the pH was carefully maintained between 8.5 and 9.0 with 10% HCl solution. At the end of the addition, when the pH remained constant between 8.5 and 9.0, the reaction mixture was allowed to stand for 30 min. under stirring at 300 RPM. The polymer was then precipitated with 150 ml of methanol, and the mother liquor was discarded. The polymer was triturated in a blender with 150 ml methanol, filtered, washed with 2 portions of 50 ml methanol, and dry at 60° C. for 16 hours to give after grinding, compound 9a as a fine white powder.

IR(KBr): 3424, 2942, 2162, 2061, 1728, 1641, 1590, 1469, 1430, 1352, 1287, 1220, 1178, 1156, 1080, 1019, 852, 817, 763 and 711 cm$^{-1}$.

CRC=40 g/g

Gel strength (GS)=4

EXAMPLE 28

Preparation of Starch Maleate Half Ester with 0.52 Eq. Maleic Anhydride, and Crosslinked with 0.18 Eq. Triglycol Dichloride, Compound 9a 2.0 g (12.3 mmol) of wheat starch A was treated as in example 27 with triglycol dichloride (416 mg, 2.22 mmol, 0.18 eq.) and maleic anhydride (4.5 ml, 1.45 M in ethyl acetate, 6.47 mmol, 0.52 eq.) to give compound 9a as a fine white powder.

IR (KBr): 3417, 2928, 2152, 2066, 1724, 1638, 1584, 1462, 1429, 1381, 1353, 1295, 1217, 1156, 1108, 1081, 1022, 931, 900, 852, 814, 763 and 711 cm$^{-1}$.

CRC=34 g/g

Gel strength (GS)=4

EXAMPLE 29

Preparation of Starch Maleate Half Ester with 0.50 Eq. Maleic Anhydride, without Crosslinking.

3.0 g (18.52 mmol) of wheat starch A (Supercell 1201-C, ADM/Ogilvie) was suspended in 60 ml of deionized water. Under stirring, 1.23 ml 30% NaOH (9.26 mmol, 0.50 eq.) was added dropwise and the solution stirred at room temperature for 1 hour. The pH was adjusted between 8.5 and 9.0 and maleic anhydride (8.9 ml, 1.45 M in ethyl acetate, 13.0 mmol, 1.05 eq.) was slowly added followed by the same treatment reported in example 30 with 225 ml of methanol for the precipitation and 2 portions of 75 ml of methanol for washing, to give starch maleate half ester as a fine powder.

IR (KBr): 3408, 2927, 2152, 2051, 1712, 1647, 1576, 1459, 1432, 1373, 1302, 1237, 1206, 1158, 1105, 1082, 1021, 994, 928, 852, 762 and 711 cm$^{-1}$.

CRC=15 g/g

Gel strength (GS)=5

EXAMPLE 30

Preparation of Starch Maleate Half Ester with 1.50 Eq. Maleic Anhydride, and Crosslinked with 0.02 Eq. Triglycol Dichloride, Compound 9a 3.0 g (18.52 mmol) of wheat starch A (Supercell 1201-C, ADM/Ogilvie) was suspended in 60 ml of deionized water. Under stirring, 1.23 ml 30% NaOH (9.26 mmol, 0.50 eq.) was added dropwise and the solution stirred at room temperature for 1 hour. Triglycol dichloride (69 mg, 0.37 mmol, 0.02 eq.) was added and the solution was heated at 70° C. for 16 hours. After cooling to room temperature, the pH was adjusted between 8.5 and 9.0 and maleic anhydride (19.0 ml, 1.45 M in ethyl acetate, 27.8 mmol, 1.50 eq.) was slowly added followed by the same treatment reported in example 27 with 225 ml of methanol for the precipitation and 2 portions of 75 ml of methanol for washing, to give compound 9a, as a fine powder.

IR (KBr): 3409, 2937, 2157, 2076, 1724, 1638, 1583, 1428, 1351, 1279, 1219, 1177, 1158, 1077, 1020, 936, 852, 817, 764, and 713 cm$^{-1}$.

CRC=28 g/g

Gel strength (GS)=5

EXAMPLE 31

Preparation of Starch Maleate Half Ester with 1.10 Eq. Maleic Anhydride, and Crosslinked with 0.10 Eq. Triglycol Dichloride, Compound 9a 3.0 g (18.52 mmol) of wheat starch A as example 30 with triglycol dichloride (346 mg, 1.85 mmol, 0.10 eq.) and maleic anhydride (14.0 ml, 1.45 M in ethyl acetate, 20.4 mmol, 1.10 eq.), to give to give compound 9a as a fine powder.

IR (KBr): 3408, 2939, 1721, 1636, 1583, 1469, 1428, 1352, 1217, 1176, 1156, 1080, 1023, 936, 853, 818, 763 and 712 cm$^{-1}$.

CRC=51 g/g

Gel strength (GS)=4

Referring to FIG. 5 (as well as table VI) illustrate the effect of maleic anhydride (MA) and triglycol dichloride ($T_3G$—diCl) concentrations on starch derivatives' CRC. (Optimization study). The FIG. 5 (and table VI) show that pratically all experiments gives products with superabsorbency (CRC higher than 15 g/g) with a maximum of CRC of 40 g/g, when 0.05 eq of triglycol dichloride and 1.05 of maleic anhydride are used. For this experiment, an hard gel is obtained (GS of 4 from table VI). Hard gel and very hard gel superabsorbents can be obtained by crosslinking unsubstituted starch with triglycol dichloride, when the polymer is precipitated at a pH between 8.5 and 9.0. For instance, an hard gel can be obtained (CRC=19 g/g and GS=4) with 0.12 eq of triglycol dichloride and a very hard gel (CRC=17 and GS=5) can be obtained with 0.06 eq of triglycol dichloride. According to table VI, very hard gels superabsorbents are also obtained independently of the concentration of triclycol dichloride and maleic anhydride. For very hard gels, the optimum CRC of 35 g/g can be reached in two experiments, one in the upper concentrations of reactants (0.18 eq triglycol dichloride and 1.25 eq maleic anhydride), and one in the lower concentrations of reactants (0.09 eq triglycol dichloride and 0.75 eq maleic anhydride).

Referring to FIG. 6 (as well as table VII) also illustrate the effect of maleic anhydride (MA) and triglycol dichloride ($T_3G$—diCl) concentrations on starch derivatives' CRC. (Optimization study). The FIG. 6 (and table VII) show results for the optimization of CRC and GS at low concentration of reactants. All experiments give hard gels or very hard gels superabsorbents. Maleate starch without crosslinking can give very hard gel superabsorbent (CRC=20 g/g and GS=5). The highest CRC obtained is 51 g/g for a hard gel superabsorbent prepared with 0.10 eq. triglycol dichloride and 1.10 eq maleic anhydride. The optimum for a very hard gel reached a CRC of 40 g/g when 0.02 eq of triglycol dichloride and 1.30 eq of maleic anhydride are used.

We claim:

1. A cross-linked polysaccharide said cross-linked polysaccharide being a polysaccharide cross-linked by a backbone chain of atoms, said backbone chain of atoms having the formula 2

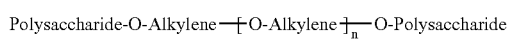

wherein each Alkylene consists of one or more unsubstituted —$CH_2$— groups, and wherein n is an integer ranging from 1 to 100.

2. A cross-linked polysacoharide as defined in claim 1 wherein n is 1, 2 or 3.

3. A cross-linked polysaccharide as defined in claim 1, wherein each Alkylene comprises from 1 to 5 —$CH_2$— groups.

4. A cross-linked polysaccharide as defined in claim 3 wherein said alkylene is a —$CH_2$—$CH_2$— group.

5. A cross-linked polysaccharide as defined in claim 4 wherein n is 1, 2 or 3.

6. A cross-linked polysaccharide as defined in claim 1, wherein said backbone chain of atoms is a group of formula Polysaccharide-O—$CH_2$—$CH_2$—O—$CH_2$—$CH_2$—O-Polysaccharide.

7. A mixture for use in a food pad; in sanitary napkins; in diapers; in incontinence products; in agricultural and forestry applications to retain water in soil and to release water to the roots of plants; in fire-fighting techniques; bandages and surgical pads; for cleanup of acidic or basic aqueous solutions spills, including water soluble chemicals spills and; as polymeric gels for cosmetics and pharmaceuticals also known as drug delivery systems and slow release substances; and for artificial snow, said mixture comprising a cross-linked polysaccharide as defined in claim 1 and one or more other known absorbents.

8. A cross-linked polysaccharide as defined in claim 1, wherein the polysaccharide is a starch selected from the group consisting of starches derived from corn, wheat, rice, potato, tapioca, waxy maize, sorghum, sago and waxy sorghum;

a modified starch selected from the group consisting of dextrinated, hydrolysed, oxidized, alkylated, hydroxyalkylated, acetylated and fractionated starches;

a member selected from the group consisting of cellulose, dextrins, polygalactomannans, ionic and/or non ionic derivatized, chitin, chitosan, alginates, xanthan gum, carageenan gum, karaya gum, arabic gum, pectin and glass-like polysaccharides; or a member selected from the group consisting of an anionic and a cationic polysaccharide.

9. A cross-linked polysaccharide as defined in claim 8 wherein the anionic polysaccharides are substituted with anionic groups selected from the group consisting of dicarboxylate and tricarboxylate groups.

10. A cross-linked polysaccharide as defined in claim 8 wherein the anionic polysaccharides are substituted with anionic groups selected from the group consisting of iminodiacetate groups and citrate groups.

11. A cross-linked polysaccharide as defined in claim 8, wherein said anionic polysaccharide is an anionic starch.

12. A cross-linked polysaccharide as defined in claim 11. wherein said anionic starch is a carboxyalkyl starch, wherein the alkyl comprises from 1 to 3 carbon atoms.

13. A cross-linked polysacchande as defined in claim 12, wherein said carboxyalkyl starch is a carboxymethyl starch.

14. A cross-linked polysaccharide as defined in claim 8, wherein said starch is a starch half ester selected from the group consisting of starch maleate half ester, starch succinate half ester, starch sulfosuccinate half ester, starch citraconate half ester, starch glutarate half ester and starch phthalate half ester.

15. A cross-linked polysaccharlde as defined in claim 1, wherein said cross-linked polysaccharide is obtained by reacting a polysacchande with an activated polyalkylene glycol having the formula 2a

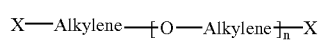

below
wherein each alkylene consists of one or more —$CH_2$— groups, wherein n is an integer ranging from 1 to 100, and wherein X is selected from the group consisting of halogen, mesylate, tosylate and triflate.

16. A cross-linked polysaccharide as defined in claim 15, wherein said halogen is selected from the group consisting of chloride, bromide and iodide.

17. A cross-linked polysaccharide as defined in claim 16, wherein said halogen is chloride.

18. A cross-linked polysaccharide as defined in claim 17, wherein said alkylene comprises from 1 to 5 —$CH_2$— groups.

19. A cross-linked polysaccharide as defined in claim 18, wherein said alkylene is an ethylene group.

20. A cross-linked polysaccharide as defined in claim 19, wherein n is 1, 2 or 3.

21. A cross-linked polysaccharide as defined in claim 15, wherein said activated polyalkylene glycol has an average molecular weight of 10,000 or less.

22. A cross-linked polysaccharide as defined in claim 21, wherein said activated polyalkylene glycol has an average molecular weight of 300 or less.

23. A cross-linked polysaccharide as defined in claim 15, wherein said activated polyalkylene glycol is selected from the group consisting of 1,5-dichloro-3-oxopentane, 1,8-dichloro-3,6-dioxooctane and 1,11-dichloro-3,6,9-trioxoundecane.

* * * * *